United States Patent [19]

Bulla et al.

[11] Patent Number: 5,693,491
[45] Date of Patent: Dec. 2, 1997

[54] **RECEPTOR FOR A *BACILLUS THURINGIENSIS* TOXIN**

[75] Inventors: Lee A. Bulla; Tae Ji, both of Laramie, Wyo.

[73] Assignee: University of Wyoming, Laramie, Wyo.

[21] Appl. No.: 326,117

[22] Filed: Oct. 19, 1994

[51] Int. Cl.$^6$ .............................. C12N 15/12; C12N 5/10; C07K 14/435
[52] U.S. Cl. .................. 435/69.1; 536/23.5; 530/350; 435/325; 435/252.3; 435/254.11
[58] Field of Search ........................... 435/69.1, 70.1, 435/172.3, 252.3, 240.2, 325, 254.11; 530/350, 412, 858; 536/23.1, 23.71, 23.5; 424/405, 93.461

[56] References Cited

U.S. PATENT DOCUMENTS

| | | | |
|---|---|---|---|
| 4,675,285 | 6/1987 | Clark et al. | 435/6 |
| 5,071,654 | 12/1991 | English | 424/405 |

OTHER PUBLICATIONS

Vadlamudi et al., *Journal of Biological Chemistry*, vol. 270, No. 10 (1995) pp. 5490–5494.

MK Lee et al. (1992) Location of a Bombyx mori receptor binding region on a Bacillus thuringiensis delta–endotoxin. J. Biol. Chem. 267 (5): 3115–3121 Feb. 1992.

T Ishihara et al. (1991) Molecular cloning and expression of a cDNA encoding the secretin receptor EMBO J. 10(7): 1635–1641 1991.

Gill et al., The Mode of Action of Bacillus Thuringiensis Endotoxins; Ammu. Rev. Entomol. (1992) 37:615–36.

Hoffman et al., Specificity of Bacillus Thuringiensis δ–endotoxins is Correlated with the Presence of High–affinity Binding Sites in the Brush Border Membrane of Target Insect Midguts; Proc. Natl. Acad. Sci. USA (1988) 85:7844–7848.

Hofte, et al., Insecticidal Crystal Proteins of Bacillus Thuringiensis; Microbiological Reviews (1989) 53(2):242–255.

Vadlamudi, et al., A Specific Binding Protein from Manduca Sexta for the Insecticidal Toxin of Bacillus Thuringiensis Subsp. Berliner; J. Biol. Chem. (1993) 268(17):12334–12340.

Van Rie et al., Specificity of Bacillus Thuringiensis δ–endotoxins; Eur. J. Biochem. (1989) 186:239–247.

Van Rie et al., Receptors on the Brush Border Membrane of the Insect Midgut as Determinants of the Specificity of Bacillus Thuringiensis Belta–Endotoxins (1990) 56(5):1378–1385.

*Primary Examiner*—Stephen Walsh
*Assistant Examiner*—Claire M. Kaufman
*Attorney, Agent, or Firm*—Morrison & Foerster LLP

[57] ABSTRACT

The cDNA that encodes a glycoprotein receptor from the tobacco hornworm which binds a *Bacillus thuringiensis* toxin has been obtained and sequenced. The availability of this cDNA permits the retrieval of DNAs encoding homologous receptors in other insects and organisms as well as the design of assays for the cytotoxicity and binding affinity of potential pesticides and the development of methods to manipulate natural and/or introduced homologous receptors and, thus, to destroy target cells, tissues and/or organisms.

16 Claims, 14 Drawing Sheets

FIG. 1A

```
770   780   790   800   810   820   830   840   850
TTG   ACA   GAA   TGC   ACA   TAC   CAA   GTA   TCG   GAC   GCG   GAC   GGA   CGG   ATC   AGC   ACA   GAG   TTC   ATG   ACG   TTC   AGG   ATC   GAC   AGC   GTT   CGT   GGC   GAC
Leu   Thr   Glu   Cys   Thr   Tyr   Gln   Val   Ser   Asp   Ala   Asp   Gly   Arg   Ile   Ser   Thr   Glu   Phe   Met   Thr   Phe   Arg   Ile   Asp   Ser   Val   Arg   Gly   Asp>

860   870   880   890   900   910   920   930   940
GAG   ACC   TTC   TAC   ATC   GAA   TTC   TAC   CGG   GAA   AAT   ATC   CCC   AAC   CAA   CAG   TGG   ATG   CTA   AAT   ATG   ACC   ATA   GGC   GTT   CTC   AAC   TTC
Glu   Thr   Phe   Tyr   Ile   Glu   Phe   Tyr   Arg   Glu   Asn   Ile   Pro   Asn   Gln   Gln   Trp   Met   Leu   Asn   Met   Thr   Ile   Gly   Val   Leu   Asn   Phe>

950   960   970   980   990   1000   1010   1020   1030
GTC   ACC   AGT   CCG   CTG   CAT   ATA   TTC   AGC   GTG   ACA   GCC   CTG   GAC   TCG   CTC   CCG   AAC   ACC   CAC   ACG   GTG   ACT   ATG   ATG   CAA   GTG   GCG   AAT
Val   Thr   Ser   Pro   Leu   His   Ile   Phe   Ser   Val   Thr   Ala   Leu   Asp   Ser   Leu   Pro   Asn   Thr   His   Thr   Val   Thr   Met   Met   Gln   Val   Ala   Asn>

1040   1050   1060   1070   1080   1090   1100   1110   1120
GTG   AAC   AGC   CGT   CCG   CGC   TGG   CTG   CTG   GAG   ATC   TTC   GCT   GTC   CAA   TTT   GAA   GAG   ACA   TTC   TTC   ACA   GTG   AGG   GCG   ATC
Val   Asn   Ser   Arg   Pro   Arg   Trp   Leu   Leu   Glu   Ile   Phe   Ala   Val   Gln   Phe   Glu   Glu   Thr   Phe   Phe   Thr   Val   Arg   Ala   Ile>

1130   1140   1150   1160   1170   1180   1190   1200   1210
GAC   GGA   GAC   ACT   GAG   ATC   AAT   ATG   CCT   ATC   AAC   TAC   AGG   CTG   ATT   ACA   AAT   GAG   GAA   ATT   GAG   GCC   CTG   CCT   GGT
Asp   Gly   Asp   Thr   Glu   Ile   Asn   Met   Pro   Ile   Asn   Tyr   Arg   Leu   Ile   Thr   Asn   Glu   Glu   Ile   Glu   Ala   Leu   Pro   Gly>

1220   1230   1240   1250   1260   1270   1280   1290   1300
GTG   AAC   AGC   CGT   TTC   CTC   GTG   TCG   CCA   ATT   GCT   CGC   GAC   ACA   CTG   CAA   CGA   GAG   GTG   TTT   CCA   CTT   ACG   ATC   GTC   GCT   TAC   AAA
Val   Asn   Ser   Arg   Phe   Leu   Val   Ser   Pro   Ile   Ala   Arg   Asp   Thr   Leu   Gln   Arg   Glu   Val   Phe   Pro   Leu   Thr   Ile   Val   Ala   Tyr   Lys>

1310   1320   1330   1340   1350   1360   1370   1380   1390
GGA   AAA   AGC   GGG   GCT   GTA   TTC   ACA   TCC   ACA   AAC   GTC   ATT   GTG   ACA   GAC   CAA   AGA   CCT   ATA   CAC   AAG   GAA
Gly   Lys   Ser   Gly   Ala   Val   Phe   Thr   Ser   Thr   Asn   Val   Ile   Val   Thr   Asp   Gln   Arg   Pro   Ile   His   Lys   Glu>

1400   1410   1420   1430   1440   1450   1460   1470   1480
TAT   GAT   GAG   GCC   ATG   ATC   GCA   GAG   GAG   ACG   CCC   CTG   ACC   CTC   TTC   GAT   GTG   AAA   TTC   GGA   TTT   CAT   GAT   AAG   TTA   GGT   CAA   AAC   GCT
Tyr   Asp   Glu   Ala   Met   Ile   Ala   Glu   Glu   Thr   Pro   Leu   Thr   Leu   Phe   Asp   Val   Lys   Phe   Gly   Phe   His   Asp   Lys   Leu   Gly   Gln   Asn   Ala>
```

FIG. 1B

```
1490                1500            1510            1520            1530            1540            1550            1560            1570
 *                   *               *               *               *               *               *               *               *
CAG TAC ACG GTG CGT CTA GAG AGC GTG GAC CCT CCA GGC GCT GAG GCA TTC TAC ATA GCG CCT GAA GTC GGC TAC CAG CGA CAG ACC
Gln Tyr Thr Val Arg Leu Glu Ser Val Asp Pro Pro Gly Ala Glu Ala Phe Tyr Ile Ala Pro Glu Val Gly Tyr Gln Arg Gln Thr>

1580                1590            1600            1610            1620            1630            1640            1650            1660
 *                   *               *               *               *               *               *               *               *
TTC ATC ATG GGC ACC CTC AAT CAC TCC ATG CTG GAT TAC TTC GAA GTG AGT ATT CGG ATT ACG GAG TTA GCG AAC GAC AAC
Phe Ile Met Gly Thr Leu Asn His Ser Met Leu Asp Tyr Phe Glu Val Ser Ile Arg Ile Thr Glu Leu Ala Thr Asp Asn>

1670                1680            1690            1700            1710            1720            1730            1740            1750
 *                   *               *               *               *               *               *               *               *
AAC GAC AGG CAC GTG GGC GTC TTG GTT CAC ATT GAC AAT CTC CCA GAG TTT CAG GAT GAG CAG CCG TTC GAA CAC GCC GTA GTG CAG
Asn Asp Arg His Val Gly Val Leu Val His Ile Asp Asn Leu Pro Glu Phe Gln Asp Glu Gln Pro Phe Glu His Ala Val Val Gln>

1760                1770            1780            1790            1800            1810            1820            1830            1840
 *                   *               *               *               *               *               *               *               *
ACC GTC TTC GAC GAG ACT GAA GGC GGG TTC GTC GCC AAG GCG GTT GCA CAC GAC ATC GGG GAT GTC GAG CAT
Thr Val Phe Asp Glu Thr Glu Gly Gly Phe Val Ala Lys Ala Val Ala His Asp Ile Gly Asp Val Glu His>

1850                1860            1870            1880            1890            1900            1910            1920            1930
 *                   *               *               *               *               *               *               *               *
ACT TTA GGT AAC GCT GTT AAC TTC CTG ACC ATC GAC AAA CTC ACC GGC ATC CGC GTC TCA GCT AAC GAC TCC AAC TAC
Thr Leu Gly Asn Ala Val Asn Phe Leu Thr Ile Asp Lys Leu Thr Gly Ile Arg Val Ser Ala Asn Asp Ser Phe>

1940                1950            1960            1970            1980            1990            2000            2010            2020
 *                   *               *               *               *               *               *               *               *
CGA GAA AGT GAA TTA TTT GTG CAG GCT CGA GTG TTT GCA ACA ACG CTG CAG CAC ACG GCG ACG TCA CAG CTG GTC ATA CGA CTA
Arg Glu Ser Glu Leu Phe Val Gln Ala Arg Val Phe Ala Thr Thr Leu Gln His Thr Ala Thr Ser Gln Leu Val Ile Arg Leu>

2030                2040            2050            2060            2070            2080            2090            2100            2110
 *                   *               *               *               *               *               *               *               *
AAT GAC ATC AAC AAC ACG CCA CCC ATC CTA CGG GCC AGT GAG GAG AAC GTG CCT GAT GGC CAC GTC ATC ACC
Asn Asp Ile Asn Asn Thr Pro Pro Ile Leu Arg Ala Ser Glu Glu Asn Val Pro Asp Gly His Val Ile Thr>

2120                2130            2140            2150            2160            2170            2180            2190            2200
 *                   *               *               *               *               *               *               *               *
CAG GAG TTA CGC GCC ACC GAC CCC GAC GCC ACG GAT CTG CGC TTC GAG ATA AAC TGG GAC ACC TCT TTC GCC AAG GGC CGC
Gln Glu Leu Arg Ala Thr Asp Pro Asp Ala Thr Asp Leu Arg Phe Glu Ile Asn Trp Asp Thr Ser Phe Ala Lys Gly Arg>
```

```
2210                2220      2230      2240      2250      2260      2270      2280      2290
 *                   *         *         *         *         *         *         *         *
CAG GCT AAC CCC GAC GAG TTT AGG AAT TGC GTG GAA ATC GAG ACC ATC TTC CCC GAG ATT AAC AAC CGG GGA CTG GCT ATC GGC GTT
Gln Ala Asn Pro Asp Glu Phe Arg Asn Cys Val Glu Ile Glu Thr Ile Phe Pro Glu Ile Asn Asn Arg Gly Leu Ala Ile Gly Val>

2300                2310      2320      2330      2340      2350      2360      2370      2380
 *                   *         *         *         *         *         *         *         *
GTA GCG CGC GAA ATC AGA CAC AAC GTG ACC ATA GAC TAC GAG TTT GAG GTC CTC ACA TCC CTC GTG AGG GTG CGT GAC CTT AAC ACC
Val Ala Arg Glu Ile Arg His Asn Val Thr Ile Asp Tyr Glu Phe Glu Val Leu Thr Ser Leu Val Arg Val Arg Asp Leu Asn Thr>

2390                2400      2410      2420      2430      2440      2450      2460      2470
 *                   *         *         *         *         *         *         *         *
GTC TAC GGA GAC GAC TAC GAC ATG CTC GAA TCG GAA GAC TAC ATA ATC GAT GAC AAC GCG CCG GTG TGG GTG GAG GGG ACT CTG
Val Tyr Gly Asp Asp Tyr Asp Met Leu Glu Ser Glu Asp Tyr Ile Ile Asp Asn Ala Pro Val Trp Val Glu Gly Thr Leu>

2480                2490      2500      2510      2520      2530      2540      2550      2560
 *                   *         *         *         *         *         *         *         *
GAG CAG AAC TTC CGA GTC GTC CGC GAG ATG GGC GGG CTC GTG GTG TCC GGC CGC GCG GAC GAC ATC ACG CCG GGA CCG CTC TAC AAC
Glu Gln Asn Phe Arg Val Val Arg Glu Met Ser Ala Gly Leu Val Val Ser Gly Arg Ala Asp Asp Ile Thr Pro Gly Pro Leu Tyr Asn>

2570                2580      2590      2600      2610      2620      2630      2640      2650
 *                   *         *         *         *         *         *         *         *
CAA GTG CGA TAC ACC ATT TTC CCT CGT GAA GAC ACA GAT AAG CTG ATA ATG ATC CAC TTC CTC ACG GGT CAA ATT TCC GTG AAC ACA
Gln Val Arg Tyr Thr Ile Phe Pro Arg Glu Asp Thr Asp Lys Leu Ile Met Ile His Phe Leu Thr Gly Gln Ile Ser Val Asn Thr>

2660                2670      2680      2690      2700      2710      2720      2730      2740
 *                   *         *         *         *         *         *         *         *
AGC GGC GCC ATC GAC GCG GAT ACT CCA CGC TTC CAC CTC TAC TAT ACA GTG GTC GCT AGT TGC CGA GAA GAT CCT GCA
Ser Gly Ala Ile Asp Ala Asp Thr Pro Arg Phe His Leu Tyr Tyr Thr Val Val Ala Ser Asp Arg Cys Glu Asp Pro Ala>

2750                2760      2770      2780      2790      2800      2810      2820      2830      2840      2850
 *                   *         *         *         *         *         *         *         *         *
GAT TGC CCC CCT GAC ACT CCG ACT TAT TGG GAA ACC AAT ATC ACA CAC ATC ACC GAC AAC ACG TCG ACA GAG GTC CCG CAG GCG GAA
Asp Cys Pro Pro Asp Thr Pro Thr Tyr Trp Glu Thr Asn Ile Thr His Ile Thr Asp Asn Asn Lys Val Pro Gln Ala Glu>

2840                2850      2860      2870      2880      2890      2900      2910      2920
 *                   *         *         *         *         *         *         *         *
ACG ACT AAG TTC GAT ACC GTC GTG TAT ATT TAC GAG AAC GCA ACC CAC TTA GAC GAG GTG ACT CTG ATA AGT GCC GAT CTT GAC AGA
Thr Thr Lys Phe Asp Thr Val Val Tyr Ile Tyr Glu Asn Ala Thr His Leu Asp Glu Val Thr Leu Ile Ser Ala Asp Leu Asp Arg>
```

FIG. 1E

```
2930                 2940                 2950                 2960                 2970                 2980                 2990                 3000                 3010
GAC  GAA  ATA  TAC  CAC  ACG  GTG  AGC  TAC  ATC  AAT  TAT  GCA  AAT  CCT  CGA  CTG  ATG  AAC  TTC  TCC  GTG  AAC  GAG  ACC
Asp  Glu  Ile  Tyr  His  Thr  Val  Ser  Tyr  Ile  Asn  Tyr  Ala  Asn  Pro  Arg  Leu  Met  Asn  Phe  Ser  Val  Asn  Arg  Thr 3020                 3030                 3040                 3050                 3060                 3070                 3080                 3090                 3100
CTG  TAC  GTG  GAC  TAT  GAG  ACC  CAG  GGT  AGT  GGC  GAG  GTG  GAC  CGT  CGT  GAT  GAA  CCA  CAC  CGT  ATC  TTC  AAC
Leu  Tyr  Val  Asp  Tyr  Glu  Thr  Gln  Gly  Ser  Gly  Glu  Val  Asp  Arg  Arg  Asp  Glu  Pro  His  Arg  Ile  Phe  Asn 3110                 3120                 3130                 3140                 3150                 3160                 3170                 3180                 3190
ATC  GAC  AAC  TTC  ATG  GGG  GAA  GGA  GAA  AAT  CAG  AAC  GAC  ACA  GAA  GTT  CTC  GTT  ATC  TTG  GAT  GTG  AAT  GAC  AAT
Ile  Asp  Asn  Phe  Met  Gly  Glu  Gly  Glu  Asn  Gln  Asn  Asp  Thr  Glu  Val  Leu  Val  Ile  Leu  Asp  Val  Asn  Asp  Asn 3200                 3210                 3220                 3230                 3240                 3250                 3260                 3270                 3280
CCT  GAA  TTG  CCA  CCG  CCG  AGC  GAA  CTC  TCT  ACT  ATA  GAG  TCT  AAG  CAG  GGC  GTC  CTT  GAA  GAG  ATC  TTC  GCC
Pro  Glu  Leu  Pro  Pro  Pro  Ser  Glu  Leu  Ser  Thr  Ile  Glu  Ser  Lys  Gln  Gly  Val  Leu  Glu  Glu  Ile  Phe  Ala 3290                 3300                 3310                 3320                 3330                 3340                 3350                 3360                 3370
GAC  CGC  GAG  CCC  GAC  ACA  GAC  AAC  TCC  AGG  TAC  GAG  AAC  CTG  CTG  AGC  ACG  GAG  ATC  GAA  GTG
Asp  Arg  Glu  Pro  Asp  Thr  Asp  Asn  Ser  Arg  Tyr  Glu  Asn  Leu  Leu  Ser  Thr  Glu  Ile  Glu  Val 3380                 3390                 3400                 3410                 3420                 3430                 3440                 3450                 3460
TTT  GTG  ATG  ATA  CAG  ATC  GCG  AAC  GTC  GAG  CTG  GAG  ACC  ATG  GCC  ATG  GAC  CTG  AAG  GGA  TAT  TGG  GGG  ACG  TAC
Phe  Val  Met  Ile  Gln  Ile  Ala  Asn  Val  Glu  Leu  Glu  Thr  Met  Ala  Met  Asp  Leu  Lys  Gly  Tyr  Trp  Gly  Thr  Tyr 3470                 3480                 3490                 3500                 3510                 3520                 3530                 3540                 3550
CGG  GCA  TTC  GAC  CAC  GGC  ATT  CCG  CAA  ATG  TCC  AAC  GAG  ACA  TAT  GAG  ATC  CAT  CCG  AAC  TAC  GCG
Arg  Ala  Phe  Asp  His  Gly  Ile  Pro  Gln  Met  Ser  Asn  Glu  Thr  Tyr  Glu  Ile  His  Pro  Asn  Tyr  Ala 3560                 3570                 3580                 3590                 3600                 3610                 3620                 3630                 3640
GTC  TTC  CCG  AAC  GAT  GCC  CTT  CGA  ATA  GCT  GTA  ATC  AAT  GGA  GTT  CTA  GCG  ACA  AAC  GGA
Val  Phe  Pro  Asn  Asp  Ala  Leu  Arg  Ile  Ala  Val  Ile  Asn  Gly  Val  Leu  Ala  Thr  Asn  Gly
```

```
3650        3660            3670            3680            3690            3700            3710            3720            3730
GAG CGG ATA TCG GCG ACT GAT CCG GAC GGA CTC CAC GCG GGC GTC GTG ACC TTC CAA GTG GTA GGC GAT GAG GAA TCA CAA CGG TAC TTT
Glu Arg Ile Ser Ala Thr Asp Pro Asp Gly Leu His Ala Gly Val Val Thr Phe Gln Val Val Gly Asp Glu Glu Ser Gln Arg Tyr Phe>

3740        3750            3760            3770            3780            3790            3800            3810            3820
CAA GTT AAC GAT GGC GAG AAC CTC GGC TCG TTG AGG TTA CTG CAA GCC GTT CCA GAG GAG ATC AGG GAG TTC CGG ATA ACG ATT CGC
Gln Val Asn Asp Gly Glu Asn Leu Gly Ser Leu Arg Leu Leu Gln Ala Val Pro Glu Glu Ile Arg Glu Phe Arg Ile Thr Ile Arg>

3830        3840            3850            3860            3870            3880            3890            3900            3910
GCT ACA GAC CAG GGA GAC CCA GGA CTG TCC ACG GAC ATG ACG TTC GTT TTT GTG CCC ACG CAA GGA GAA CCT AGA TTC
Ala Thr Asp Gln Gly Asp Pro Gly Leu Ser Thr Asp Met Thr Phe Val Phe Val Pro Thr Gln Gly Glu Pro Arg Phe>

3920        3930            3940            3950            3960            3970            3980            3990            4000
GCA TCC TCA GAA CAT GTC GCT GCT TTC ATA GAA AAG TAC TTC GCC ATG GAA GAG TCT CAC CAA CTT GCA CAA CAA GAC ATC AAG AAC
Ala Ser Ser Glu His Val Ala Ala Phe Ile Glu Lys Tyr Phe Ala Met Glu Glu Ser His Gln Leu Ala Gln Gln Asp Ile Lys Asn>

4010        4020            4030            4040            4050            4060            4070            4080            4090
CAT CTC TGT GAC GAC TGT CAC AGC ATT ATT CGT ATT GCC GGT ATG GGC AAC AGC GAG GGT CAT TTC GGC CTG GAT CCT GTT CGC AAC
His Leu Cys Asp Asp Cys His Ser Ile Ile Arg Ile Ala Gly Met Gly Asn Ser Glu Gly His Phe Gly Leu Asp Pro Val Arg Asn>

4100        4110            4120            4130            4140            4150            4160            4170            4180
AGG TTG CTG AAG AAG CTT AGA GAG GAG ATA CTG AGG GCC TCC CAC ACT CTG CAA GTG GCG GCT AGT AAC TCG CCC GAT GGT GGC ATT
Arg Leu Leu Lys Lys Leu Arg Glu Glu Ile Leu Arg Ala Ser His Thr Leu Gln Val Ala Ala Ser Asn Ser Pro Asp Gly Gly Ile>

4190        4200            4210            4220            4230            4240            4250            4260            4270
CCA CTT CCT TCC ATC GGC AGA ACT GTT GTG AGG GAG GCA GAC CCT CGT CCA GTG TTT GAA AGG TAC CCC GAT ACC GCA
Pro Leu Pro Ser Ile Gly Arg Thr Val Thr Val Arg Glu Ala Asp Pro Arg Pro Val Phe Glu Arg Tyr Pro Asp Thr Ala>

4280        4290            4300            4310            4320            4330            4340            4350            4360
ATA TCC ACA GCG GAC TCC ATC GGC AGA GAG CTG CTG AGA TTA CAT GCG GAC CAG TCT GAA GGC TCG GCC ATT ACT TAT GCT ATA GAC TAC
Ile Ser Thr Ala Asp Ser Ile Gly Arg Glu Leu Leu Arg Leu His Ala Asp Gln Ser Glu Gly Ser Ala Ile Thr Tyr Ala Ile Asp Tyr>
```

FIG. IF

```
4370                    4380                    4390                    4400                    4410                    4420                    4430                    4440                    4450
  *                       *                       *                       *                       *                       *                       *                       *                       *
GAT ACA ATG GTA GTG GAC CCC AGC CTG GAG GCA GTG AGA CAG TCG GCT TTC GTA CTG AAC GCT CAA ACC GGA GTG CTG ACG CTT AAT ATC
Asp Thr Met Val Val Asp Pro Ser Leu Glu Ala Val Arg Gln Ser Ala Phe Val Leu Asn Ala Gln Thr Gly Val Leu Thr Leu Asn Ile>

4460                    4470                    4480                    4490                    4500                    4510                    4520                    4530                    4540
  *                       *                       *                       *                       *                       *                       *                       *                       *
CAG CCC ACG ACG ATG GGA CTT GCA TTC GAA GTC ACA GCT GAC ACG GCC GGC GCT CAG GAC CGC ACC GAC GTC ACC GTG
Gln Pro Thr Thr Met Gly Leu Ala Phe Lys Phe Glu Val Thr Ala Asp Thr Ala Gly Ala Gln Asp Arg Thr Asp Val Thr Val>

4550                    4560                    4570                    4580                    4590                    4600                    4610                    4620                    4630
  *                       *                       *                       *                       *                       *                       *                       *                       *
TAC GTG GTA TCC TCG CAG AAC CGC GTC TTC TAC TTC GTG GTG TTC GTC AAC ACG CTG CAA CAG GTC GAA GAC AAC AGA GAC TTT ATC GCG GAC ACC
Tyr Val Val Ser Ser Gln Asn Arg Val Phe Tyr Phe Val Val Phe Val Asn Thr Leu Gln Gln Val Glu Asp Asn Arg Asp Phe Ile Ala Asp Thr>

4640                    4650                    4660                    4670                    4680                    4690                    4700                    4710                    4720
  *                       *                       *                       *                       *                       *                       *                       *                       *
TTC AGC GCT GGG TTC AAC ATG ACC TGC AAC ATC GAC CAA CAG GTG GTG CCC AAC GAC CCC GTC ACC GGC GTG GCG CTG GAG CAC AGC ACG
Phe Ser Ala Gly Phe Asn Met Thr Cys Asn Ile Asp Gln Gln Val Val Pro Asn Asp Pro Val Thr Gly Val Ala Leu Glu His Ser Thr>

4730                    4740                    4750                    4760                    4770                    4780                    4790                    4800                    4810                    4820                    4830
  *                       *                       *                       *                       *                       *                       *                       *                       *                       *                       *
CAG ATG GCC ACT TCA TAC GGG ACA ACG TAC CCG TAC TCG CTG ATG AGA TAG A ACAGATCCGTAGTGACTAGTCCTCCTGAGCTCGATACAAACAACG
Gln Met Ala Thr Ser Tyr Gly Thr Thr Tyr Pro Tyr Ser Leu Met Arg *** Xxx 4840                    4850                    4860                    4870                    4880                    4890                    4900                    4910                    4920                    4930                    4940                    4950
  *                       *                       *                       *                       *                       *                       *                       *                       *                       *                       *                       *
CTGGCGCGCGATCGTGGTGTTGCAGGACTTGTTGACCAACTCCAGCCCGGGACTTCGGCGCCTGACTCGAGCCTGACTCTGGCCTCTACGTCTGCACGGTGTACGTCTGTCTGTGTCTCGGTTTCATG 4960        4970        4998        4990        5000        5010        5020        5030        5040        5050        5060        5070
  *           *           *           *           *           *           *           *           *           *           *           *
TGCCTTGTGCTACTGCTTACCTTCATCATCAGGACTACACCGCTAAACCGAGCGGTTGGAAGCCCTGTCGATGACGAAGTACGGCTCACTGGACTCTGGATTGAACCGGCCGGCATCGCC 5080        5090        5100        5110        5120        5130        5140        5150        5160        5170        5180        5190
  *           *           *           *           *           *           *           *           *           *           *           *
GCCCCGGCACCAACAAACACTGTGGAAGGCTCCAACCCTATCTTCAATGAAGCAATAAAGAGCCAGATTTAGATGCCATTAGCGAGGGTTCCAACGACTCTGATCTGATCGGCATC
```

FIG. IG

```
5200        5210        5220        5230        5240        5250        5260        5270        5280        5290        5300        5310
  *           *           *           *           *           *           *           *           *           *           *           *
GAAGATCTTGCGCACTTTGGCAACGTCTTCATGGATCCTGAGGTGAACGAAAAGGCAAATGGTTATCCCGAAGTCGCAAACCACACAACTTCGCTTTCAACCCGACTCCCTTCTCG 5320        5330        5340        5350        5360        5370        5380        5390        5400        5410        5420        5430
  *           *           *           *           *           *           *           *           *           *           *           *
CCTGAGTTCGTTAACGGACAGTTCAGAAGATCTAGAAGATAACACACTAGTTAAGATCATTAATTTTGGAGTTTGGAATTAAGATTTTGAAAGGATAGTTGTGATAAGCCTGTGATT 5440        5450        5460        5470        5480        5490        5500        5510        5520        5530        5540        5550
  *           *           *           *           *           *           *           *           *           *           *           *
TTTAAAACTGTAATTGAAAAAAAAATTGAGACCTCCATTTAAGCTCTTGCTCTCATCTCATCAAATTTTATAAAATGCCATTAGTCATTAAGATACTCGATTAATTTAAGATTATTTA 5560        5570
  *           *
AGATATTATGTAAAATAAATATATTGTC
```

FIG. 1H

Met Ala Val Asp Val Arg Ile Ala Ala Phe Leu Leu Val Phe Ile Ala
1           5                   10                      15

Pro Ala Val Leu Ala Gln Glu Arg Cys Gly Tyr Met Thr Ala Ile Pro
            20                  25                  30

Arg Leu Pro Arg Pro Asp Asn Leu Pro Val Leu Asn Phe Glu Gly Gln
        35                  40                  45

Thr Trp Ser Gln Arg Pro Leu Leu Pro Ala Pro Glu Arg Asp Asp Leu
    50                  55                  60
                                Cad1 →

Cys Met Asp Ala Tyr His Val Ile Thr Ala Asn Leu Gly Thr Gln Val
65              70                  75                      80

Ile Tyr Met Asp Glu Glu Ile Glu Asp Glu Ile Thr Ile Ala Ile Leu
            85              90                      95

Asn Tyr Asn Gly Pro Ser Thr Pro Phe Ile Glu Leu Pro Phe Leu Ser
            100                 105             110

Gly Ser Tyr Asn Leu Leu Met Pro Val Ile Arg Arg Val Asp Asn Gly
        115                 120                 125

Ser Ala Ser His His His Ala Arg Gln His Tyr Glu Leu Pro Gly Met
    130             135                 140

Gln Gln Tyr Met Phe Asn Val Arg Val Asp Gly Gln Ser Leu Val Ala
145             150                 155                     160

Gly Val Ser Leu Ala Ile Val Asn Ile Asp Asp Asn Ala Pro Ile Ile
            165                 170                 175
        Cad2 →

Gln Asn Phe Glu Pro Cys Arg Val Pro Glu Leu Gly Glu Pro Gly Leu
            180                 185                 190

Thr Glu Cys Thr Tyr Gln Val Ser Asp Ala Asp Gly Arg Ile Ser Thr
        195             200                 205

Glu Phe Met Thr Phe Arg Ile Asp Ser Val Arg Gly Asp Glu Glu Thr
    210                 215                 220

Phe Tyr Ile Glu Arg Thr Asn Ile Pro Asn Gln Trp Met Trp Leu Asn
225                 230                 235                 240

Met Thr Ile Gly Val Asn Thr Ser Leu Asn Phe Val Thr Ser Pro Leu
            245                 250                 255

His Ile Phe Ser Val Thr Ala Leu Asp Ser Leu Pro Asn Thr His Thr
        260                 265                 270

Val Thr Met Met Val Gln Val Ala Asn Val Asn Ser Arg Pro Pro Arg
    275                 280                 285

FIG. 2A

```
              Cad3
      ┌─────────────────────▶
Trp  Leu  Glu  Ile  Phe  Ala  Val  Gln  Gln  Phe  Glu  Glu  Lys  Ser  Tyr  Gln
     290                 295                 300

Asn  Phe  Thr  Val  Arg  Ala  Ile  Asp  Gly  Asp  Thr  Glu  Ile  Asn  Met  Pro
305                 310                 315                           320

Ile  Asn  Tyr  Arg  Leu  Ile  Thr  Asn  Glu  Glu  Asp  Thr  Phe  Phe  Ser  Ile
               325                 330                      335

Glu  Ala  Leu  Pro  Gly  Gly  Lys  Ser  Gly  Ala  Val  Phe  Leu  Val  Ser  Pro
               340                 345                      350

Ile  Asp  Arg  Asp  Thr  Leu  Gln  Arg  Glu  Val  Phe  Pro  Leu  Thr  Ile  Val
               355                 360                      365

Ala  Tyr  Lys  Tyr  Asp  Glu  Glu  Ala  Phe  Ser  Thr  Ser  Thr  Asn  Val  Val
     370                 375                 380
                                                                Cad4
                                                        ┌───────────────▶
Ile  Ile  Val  Thr  Asp  Ile  Asn  Asp  Gln  Arg  Pro  Glu  Pro  Ile  His  Lys
385                 390                 395                           400

Glu  Tyr  Arg  Leu  Ala  Ile  Met  Glu  Glu  Thr  Pro  Leu  Thr  Leu  Asn  Phe
               405                 410                           415

Asp  Lys  Glu  Phe  Gly  Phe  His  Asp  Lys  Asp  Leu  Gly  Gln  Asn  Ala  Gln
               420                 425                      430

Tyr  Thr  Val  Arg  Leu  Glu  Ser  Val  Asp  Pro  Pro  Gly  Ala  Ala  Glu  Ala
               435                 440                      445

Phe  Tyr  Ile  Ala  Pro  Glu  Val  Gly  Tyr  Gln  Arg  Gln  Thr  Phe  Ile  Met
     450                 455                 460

Gly  Thr  Leu  Asn  His  Ser  Met  Leu  Asp  Tyr  Glu  Val  Pro  Glu  Phe  Gln
465                      470                 475                      480

Ser  Ile  Thr  Ile  Arg  Val  Val  Ala  Thr  Asp  Asn  Asn  Asp  Thr  Arg  His
               485                 490                           495
              Cad5
      ┌─────────────────────▶
Val  Gly  Val  Ala  Leu  Val  His  Ile  Asp  Leu  Ile  Asn  Trp  Asn  Asp  Glu
               500                 505                      510

Gln  Pro  Ile  Phe  Glu  His  Ala  Val  Gln  Thr  Val  Thr  Phe  Asp  Glu  Thr
               515                 520                 525

Glu  Gly  Glu  Gly  Phe  Phe  Val  Ala  Lys  Ala  Val  Ala  His  Asp  Arg  Asp
     530                 535                 540

Ile  Gly  Asp  Val  Val  Glu  His  Thr  Leu  Leu  Gly  Asn  Ala  Val  Asn  Phe
545                 550                 555                           560
```

FIG. 2B

Leu Thr Ile Asp Lys Leu Thr Gly Asp Ile Arg Val Ser Ala Asn Asp
                565                 570                 575
Ser Phe Asn Tyr His Arg Glu Ser Glu Leu Phe Val Gln Val Arg Ala
                580                 585                 590
Thr Asp Thr Leu Gly Glu Pro Phe His Thr Ala Thr Ser Gln Leu Val
                595                 600                 605
                                                              ┌─Cad6──▶
Ile Arg Leu Asn Asp Ile Asn Asn Thr Pro Pro Thr Leu Arg Leu Pro
                610                 615                 620
Arg Gly Ser Pro Gln Val Glu·Glu Asn Val Pro Asp Gly His Val Ile
625                 630                 635                 640
Thr Gln Glu Leu Arg Ala Thr Asp Pro Asp Thr Thr Ala Asp Leu Arg
                645                 650                 655
Phe Glu Ile Asn Trp Asp Thr Ser Phe Ala Thr Lys Gln Gly Arg Gln
                660                 665                 670
Ala Asn Pro Asp Glu Phe Arg Asn Cys Val Glu Ile Glu Thr Ile Phe
            675                 680                 685
Pro Glu Ile Asn Asn Arg Gly Leu Ala Ile Gly Arg Val Val Ala Arg
            690                 695                 700
Glu Ile Arg His Asn Val Thr Ile Asp Tyr Glu Glu Phe Glu Val Leu
705                 710                 715                 720
Ser Leu Thr Val Arg Val Arg Asp Leu Asn Thr Val Tyr Gly Asp Asp
                725                 730                 735
Tyr Asp Glu Ser Met Leu Thr Ile Thr Ile Ile Asp Met Asn Asp Asn
            740                 745                 750
            ┌───CAD7────────────────▶
Ala Pro Val Trp Val Glu Gly Thr Leu Glu Gln Asn Phe Arg Val Arg
        755                 760                 765
Glu Met Ser Ala Gly Gly Leu Val Val Gly Ser Val Arg Ala Asp Asp
    770                 775                 780
Ile Asp Gly Pro Leu Tyr Asn Gln Val Arg Tyr Thr Ile Phe Pro Arg
785                 790                 795                 800
Glu Asp Thr Asp Lys Asp Leu Ile Met Ile Asp Phe Leu Thr Gly Gln
            805                 810                 815
Ile Ser Val Asn Thr Ser Gly Ala Ile Asp Ala Asp Thr Pro Pro Arg
            820                 825                 830
Phe His Leu Tyr Tyr Thr Val Val Ala Ser Asp Arg Cys Ser Thr Glu
        835                 840                 845

FIG. 2C

```
Asp Pro Ala Asp Cys Pro Asp Pro Thr Tyr Trp Glu Thr Glu Gly
850             855             860
Asn Ile Thr Ile His Ile Thr Asp Thr Asn Asn Lys Val Pro Gln Ala
865             870             875             880
  Cad8
┌─────────▶
Glu Thr Thr Lys Phe Asp Thr Val Val Tyr Ile Tyr Glu Asn Ala Thr
            885             890             895
His Leu Asp Glu Val Val Thr Leu Ile Ala Ser Asp Leu Asp Arg Asp
            900             905             910
Glu Ile Tyr His Thr Val Ser Tyr Val Ile Asn Tyr Ala Val Asn Pro
        915             920             925
Arg Leu Met Asn Phe Phe Ser Val Asn Arg Glu Thr Gly Leu Val Tyr
    930             935             940
Val Asp Tyr Glu Thr Gln Gly Ser Gly Glu Val Leu Asp Arg Asp Gly
945             950             955             960
Asp Glu Pro Thr His Arg Ile Phe Phe Asn Leu Ile Asp Asn Phe Met
            965             970             975
Gly Glu Gly Glu Gly Asn Arg Asn Gln Asn Asp Thr Glu Val Leu Val
        980             985             990
                                                Cad9
                                            ┌─────────▶
Ile Leu Leu Asp Val Asn Asp Asn Ala Pro Glu Leu Pro Pro Pro Ser
        995             1000            1005
Glu Leu Ser Trp Thr Ile Ser Glu Asn Leu Lys Gln Gly Val Arg Leu
    1010            1015            1020
Glu Pro His Ile Phe Ala Pro Asp Arg Asp Glu Pro Asp Thr Asp Asn
1025            1030            1035            1040
Ser Arg Val Gly Tyr Glu Ile Leu Asn Leu Ser Thr Glu Arg Asp Ile
            1045            1050            1055
Glu Val Pro Glu Leu Phe Val Met Ile Gln Ile Ala Asn Val Thr Gly
        1060            1065            1070
Glu Leu Glu Thr Ala Met Asp Leu Lys Gly Tyr Trp Gly Thr Tyr Ala
    1075            1080            1085
Ile His Ile Arg Ala Phe Asp His Gly Ile Pro Gln Met Ser Met Asn
    1090            1095            1100
Glu Thr Tyr Glu Leu Ile Ile His Pro Phe Asn Tyr Tyr Ala Pro Glu
1105            1110            1115            1120
```

FIG. 2D

Cad10 →

Phe Val Phe Pro Thr Asn Asp Ala Val Ile Arg Leu Ala Arg Glu Arg
              1125           1130              1135

Ala Val Ile Asn Gly Val Leu Ala Thr Val Asn Gly Glu Phe Leu Glu
            1140             1145              1150

Arg Ile Ser Ala Thr Asp Pro Asp Gly Leu His Ala Gly Val Val Thr
            1155             1160             1165

Phe Gln Val Val Gly Asp Glu Glu Ser Gln Arg Tyr Phe Gln Val Val
    1170             1175             1180

Asn Asp Gly Glu Asn Leu Gly Ser Leu Arg Leu Leu Gln Ala Val Pro
1185             1190             1195             1200

Glu Glu Ile Arg Glu Phe Arg Ile Thr Ile Arg Ala Thr Asp Gln Gly
                1205             1210             1215

Thr Asp Pro Gly Pro Leu Ser Thr Asp Met Thr Phe Arg Val Val Phe
            1220             1225             1230

Cad11 →

Val Pro Thr Gln Gly Glu Pro Arg Phe Ala Ser Ser Glu His Ala Val
            1235             1240             1245

Ala Phe Ile Glu Lys Ser Ala Gly Met Glu Glu Ser His Gln Leu Pro
            1250             1255             1260

Leu Ala Gln Asp Ile Lys Asn His Leu Cys Glu Asp Asp Cys His Ser
1265             1270             1275             1280

Ile Tyr Tyr Arg Ile Ile Asp Gly Asn Ser Glu Gly His Phe Gly Leu
                1285             1290             1295

Asp Pro Val Arg Asn Arg Leu Phe Leu Lys Lys Glu Leu Ile Arg Glu
            1300             1305             1310

Gln Ser Ala Ser His Thr Leu Gln Val Ala Ala Ser Asn Ser Pro Asp
        1315             1320             1325

Gly Gly Ile Pro Leu Pro Ala Ser Ile Leu Thr Val Thr Val Thr Val
    1330             1335             1340

Arg Glu Ala Asp Pro Arg Pro Val Phe Val Arg Glu Leu Tyr Thr Ala
1345             1350             1355             1360

Gly Ile Ser Thr Ala Asp Ser Ile Gly Arg Glu Leu Leu Arg Leu His
            1365             1370             1375

Ala Thr Gln Ser Glu Gly Ser Ala Ile Thr Tyr Ala Ile Asp Tyr Asp
        1380             1385             1390

FIG. 2E

Thr Met Val Val Asp Pro Ser Leu Glu Ala Val Arg Gln Ser Ala Phe
      1395                  1400                1405

Val Leu Asn Ala Gln Thr Gly Val Leu Thr Leu Asn Ile Gln Pro Thr
    1410                1415               1420

Ala Thr Met His Gly Leu Phe Lys Phe Glu Val Thr Ala Thr Asp Thr
1425                1430              1435              1440

Ala Gly Ala Gln Asp Arg Thr Asp Val Thr Val Tyr Val Val Ser Ser
            1445              1450              1455

Gln Asn Arg Val Tyr Phe Val Phe Val Asn Thr Leu Gln Gln Val Glu
        1460              1465              1470

Asp Asn Arg Asp Phe Ile Ala Asp Thr Phe Ser Ala Gly Phe Asn Met
    1475                1480               1485

Thr Cys Asn Ile Asp Gln Val Val Pro Ala Asn Asp Pro Val Thr Gly
   1490                1495              1500

Val Ala Leu Glu His Ser Thr Gln Met Ala Ala Thr Ser Tyr Gly Thr
1505                1510              1515              1520

Thr Tyr Pro Tyr Ser Leu Met Arg
            1525

FIG. 2F

RECEPTOR FOR A *BACILLUS THURINGIENSIS* TOXIN

ACKNOWLEDGEMENT OF GOVERNMENT SUPPORT

Work resulting in the present invention was supported in part by Research Agreement 58-319R-3-011 from the Office of International Cooperation and Development, U.S.D.A. and by Cooperative Agreement 58-5410-1-135 from the Arthropod-Borne Animal Disease Laboratory, Agricultural Research Service, U.S.D.A. and by Grant HD-18702 from the National Institutes of Health. The U.S. government has certain rights in this invention.

TECHNICAL FIELD

The invention relates to receptors that bind toxins from *Bacillus thuringiensis* and thus to pesticides and pest resistance. More particularly, the invention concerns recombinantly produced receptors that bind BT toxin and to their use in assays for improved pesticides, as well as in mediation of cell and tissue destruction, dissociation, dispersion, cell-to-cell association, and changes in morphology.

BACKGROUND ART

It has long been recognized that the bacterium *Bacillus thuringiensis* (BT) produces bacteriocidal proteins that are toxic to a limited range of insects, mostly in the orders Lepidoptera, Coleoptera and Diptera. Advantage has been taken of these toxins in controlling pests, mostly by applying bacteria to plants or transforming plants themselves so that they generate the toxins by virtue of their transgenic character. The toxins themselves are glycoprotein products of the cry gene as described by Höfte, H. et al. *Microbiol Rev* (1989) 53:242. It has been established that the toxins function in the brush border of the insect midgut epithelial cells as described by Gill, S. S. et al. *Annu Rev Entomol* (1992) 37:615. Specific binding of BT toxins to midgut brush border membrane vesicles has been reported by Hofmann, C. et al. *Proc Natl Acad Sci USA* (1988) 85:7844; Van Rie, J. et al. *Eur J Biochem* (1989) 186:239; and Van Rie, J. et al. *Appl Environ Microbiol* (1990) 56:1378.

Presumably, the toxins generated by BT exert their effects by some kind of interaction with receptors in the midgut. The purification of a particular receptor from *Manduca sexta* was reported by the present inventors in an article by Vadlamudi, R. K. et al. *J Biol Chem* (1993) 268:12334. In this report, the receptor protein was isolated by immunoprecipitating toxin-binding protein complexes with toxin-specific antisera and separating the complexes by SDS-PAGE followed by electroelution. However, to date, there has been no structural information concerning any insect receptor which binds BT toxin, nor have, to applicants' knowledge, any genes encoding these receptors been recovered.

DISCLOSURE OF THE INVENTION

The invention provides recombinant materials for the production of BT toxin-binding receptors as well as methods to employ these materials to generate receptors for use in screening assays for candidate pesticides. Since the native cDNA sequence encoding this receptor, designated BT-R$_1$, has been retrieved from the tobacco hornworm, encoding DNA for receptors in other species of insects, as well as in other organisms, which have homology to hornworm receptor can be obtained.

Thus, in one aspect, the invention is directed to a polynucleotide in purified and isolated form which comprises a nucleotide sequence encoding a receptor that binds a BT toxin and other ligands and which has the requisite homology to the BT-R$_1$ protein.

In other aspects, the invention is directed to expression systems for nucleotide sequences encoding the receptor, to methods of producing the receptor recombinantly, to the receptor as thus produced, to antibodies specifically immunoreactive with the receptor, to assay methods useful for screening candidate pesticides, to antisense polynucleotides corresponding to the coding sequence, to methods of targeting tissues and/or cells using the binding characteristics of the receptor, and to methods of manipulating tissues and/or cells using the function of the receptor.

BRIEF DESCRIPTION OF THE DRAWINGS

FIGS. 1A–1F (SEQ ID NO:1 and SEQ ID NO:2) show the nucleotide sequence and deduced amino acid sequence of cDNA encoding the BT-R$_1$ protein from *M. sexta*.

FIG. 2A–2F (SEQ ID NO:2) show the cadherin motifs in the amino acid sequence of the BT-R$_1$ protein from *M. sexta*.

MODES OF CARRYING OUT THE INVENTION

The invention provides, for the first time, sequence information concerning receptors that bind BT toxins in insect midguts.

The BT-R$_1$ cDNA clone retrieved as described in the examples below encodes a protein having an identical amino acid composition with that described for the native receptor. Furthermore, toxin-binding specificity and immunoreactivity are similar. The native 210 kD BT-R$_1$ specifically recognizes cryIA(b) toxin of BT-berliner; a K$_d$ value of 708 pM was obtained for the native protein.

The cryIA(b) toxin selectively kills *M. sexta* larvae with an LC$_{50}$ of 7.5 ng/cm$^2$ of diet surface. BT-R$_1$ binds the toxin under both reducing and nonreducing conditions and protease treatment of intestinal BBMV vesicles prepared from *M. sexta* showed that a 50 kD fragment of the 210 kD receptor is sufficient for toxin binding. The 50 kD toxin-binding domain is extracellular since the intestinal BBMV vesicles are oriented predominantly right side out as reported by Haase, W. H. et al. *Biochem J* (1978) 172:57. This is consistent with the characteristics of the deduced amino acid sequence of the cDNA clone described below, as well as with the binding of toxin to the surface of intact BT-R$_1$ transfected human embryonic 293 cells as described in Example 3.

Whereas a particular cDNA clone from the tobacco hornworm has been described as illustration, the availability of this sequence information permits retrieval of corresponding receptors responsive to BT and related toxins from other species. This is conveniently accomplished by using the cDNA obtained in the present invention as a probe for screening cDNA or genomic libraries under conditions of stringency which eliminate false positives and retrieve substantially only corresponding receptors with coding sequences that are homologous to the coding sequence for the receptor of the present invention. Thus, the BT-R$_1$ protein itself and receptor proteins encoded by a nucleotide sequence homologous to the native nucleotide sequence encoding BT-R$_1$ are provided by the invention. Alternatively, PCR-mediated cloning can be used; however, this method does not take advantage of the detailed and complete information that resides in the availability of the nucleotide sequence encoding the full-length receptor from

*M. sexta*. Also, PCR-mediated cloning introduces errors in natural DNA sequences. Thus, by using the full-length cDNA as a probe under conditions of appropriate stringency, only nucleotide sequences encoding the corresponding receptors will be obtained. The standard hybridization conditions include hybridization with nonspecific DNA such as salmon DNA at 50° C. and washing at 45° C. To obtain corresponding receptors having the lowest detectable homology with the receptor from *M. sexta*, the cDNA probe is hybridized under conditions of low standard stringency (30°–37° C. and 4–6× SSC. More closely related corresponding receptors are obtained by hybridizing the cDNA probe under moderate standard stringency conditions (40°–50° C. in 1× SSC). A clone containing the cDNA insert for use as a probe was deposited at the American Type Cell Culture Collection as ATCC 98713.

The distribution of receptors of appropriate homology in the animal kingdom is believed to be fairly wide. Indeed, it is thought that higher organisms such as mammals, including primates, contain corresponding receptors which are homologous to BT-R$_1$ but respond to modified forms of BT toxins. In addition, other parasites such as nematodes, both those that afflict plants and those that afflict animals, will contain corresponding receptors.

Although one of the advantages of the use of BT toxins as insecticides is its specificity for certain orders of insects, this specificity is believed to result from the particular structure of the BT toxin rather than the unavailability of a corresponding mechanism in other insect orders. Thus, modified forms of BT toxin would be effective with respect to insects which contain homologous but slightly different forms of the receptor from that of the BT-R$_1$ protein illustrated below.

As used herein, "A receptor that specifically binds a BT toxin" refers to a receptor which is homologous to the BT-R$_1$ protein illustrated herein and which binds to either BT toxins themselves or to BT toxins that are sufficiently modified so as to bind these receptors which provide the required homology to BT-R$_1$.

The criteria for inclusion of a receptor in the present invention are the requirements that 1) it behave as a receptor—i.e., be capable of being displayed at the cell membrane; 2) it be sufficiently homologous to the BT-R$_1$ receptor described herein that a nucleotide sequence encoding the protein hybridizes under the stringency conditions described above to the nucleotide sequence encoding BT-R$_1$ as contained in the plasmid deposited at the American Type Culture Collection as ATCC 98713; and 3) when displayed on the surface of a cell, it is capable of binding a BT toxin or a modified form of BT toxin that exerts a cytotoxic effect either on the cell in which the receptor resides or in a tissue with which the cell is associated.

The structural characteristics of the "modified BT toxin" are defined by the functional property set forth above, but it may be convenient to design modified forms of BT toxin by conservative amino acid substitutions or other known protein-manipulating techniques applied to naturally occurring BT toxins.

The presence of similar receptors in noninsect organisms as well as other insects besides those harboring BT-R$_1$ is supported by the sequence similarity of the BT-R$_1$ protein to that of the various members of the cadherin superfamily of proteins, which are membrane glycoproteins believed to mediate calcium-dependent cell aggregation and sorting. See, for example, Takeichi, M. *Science* (1991) 251:1451; and Takeichi, M. *N Rev Biochem* (1990) 59:237.

Included in this superfamily are desmoglien, desmocollins, the Drosophila fat tumor suppressor, human intestinal peptide transport protein and T-cadherin. All of these proteins share common extracellular motifs although their cytoplasmic domains differ. Goodwin, L. et al. *Biochem Biophys Res Commun* (1990) 173:1224; Holton, J. L. et al. *J Cell Sci* (1990) 97:239; Bestal, D. J. *J Cell Biol* (1992) 119:451; Mahoney, P. A. et al. *Cell* (1991) 853; Dantzig, A. H. et al. *Science* (1994) 264:430; and Sano, K. et al. *EMBO J* (1993) 12:2249. Inclusion of BT-R$_1$ in the cadherin superfamily is further supported by the report that EDTA decreases the binding of cryIA(b) toxin of BT to the 210 kD receptor of *M. sexta* (Martinez-Ramirez, A. C. et al. *Biochm Biophys Res Commun* (1994) 201:782Q).

It is noted below that the amino acid sequence of BT-R$_1$ reveals that a calcium-binding motif is present. This is consistent with the possibility that cells having receptors to bind toxin may themselves survive although they render the tissues in which they are included permeable to solutes and thus effect disintegration of the tissue. Such a mechanism is proposed for the death of insects that ingest the toxin via the epithelial cells in their midgut by Knowles, B. H. et al. *Biochim Biophys Acta* (1987) 924:509. Such a mechanism is also supported in part by the results set forth in Example 4 hereinbelow which indicate that the effect of the toxin on embryonic 293 cells modified to express the receptor at their surface is reversible.

Thus, in summary, the invention provides a family of receptors that is able to mediate the negative effects exerted by BT toxin or its modified forms on the cells expressing the receptor, by damaging the cells themselves and/or the tissue or organ of which the cells form a part. The receptor may be expressed natively at the surface of the target cells or the target cells may be modified to contain an expression system which will effect the display of receptor at the surface. The availability of this family of receptors and recombinant methods for its production and for the production of cells displaying it at their surfaces provides a number of opportunities to conduct screening assays for improved toxins, particularly insecticidal toxins, for generation of antibodies that can be useful as alternatives to chemotherapeutic agents for the destruction and/or dissociation of unwanted cells or tissues, and for the design of improved toxins and pharmaceuticals.

Screening Assays

The availability of the recombinant family of receptors of the present invention permits design of straightforward screening assays for toxins which will interact successfully with these receptors resulting in measurable effects on the cells in which the receptors reside. Briefly, suitable host cells, such as COS cells for transient expression, CHO cells for stable expression, and a variety of other mammalian and insect host cells can be modified to contain expression vectors appropriate to the hosts for the production of the receptors of the invention displayed on the surfaces of the cells. Since the receptors are natively membrane proteins, no particular design of the expression system is required in order to effect their disposition at the cell surface. Expression vectors suitable for any desired host are generally known in the art. For example, for mammalian expression, suitable control sequences include the SV40 and adenovirus promoters as constitutive promoters, the metallothionein inducible promoter, suitable enhancers, if desired, and termination signals and the like. For insect cells, the bacculovirus system is preferred. For other eucaryotic cells such as yeast, the glycolytic enzyme promoters and various amino acid synthesis promoters are commonly employed. Procaryotic cells such as *E. coli* also may be adapted for expression of the receptor in the assay of the invention, for instance by using a reporter gene under the control of cyclic AMP and operably linked to the receptor via protein G such that toxin binding will interrupt adenyl cyclase activity and thereby produce a detectable change in reporter gene activity. The assay system in a prokaryotic host may require further modification to compensate for lack of glycosylation which is known to occur in insect cells where the BT-$R_1$ protein is naturally expressed.

The cells are modified by transfection, retroviral infection, electroporation or other known means, to contain the desired expression system and then cultured under conditions wherein the receptor protein is produced and displayed. If desired, the cells are then recovered from the culture for use in the assay, or the culture itself can be used per se.

In the assays, the modified cells are contacted with the candidate toxin and the effect on metabolism or morphology is noted in the presence and absence of the candidate. The effect may be cytotoxic—i.e., the cells may themselves exhibit one of the indices of cell death, such as reduced thymidine uptake, slower increase in optical density of the culture, reduced exclusion of vital dyes (e.g., trypan blue), increased release of viability markers such as chromium and rubidium, and the like. The differential response between the toxin-treated cells and the cells absent the toxin is then noted. The strength of the toxin can be assessed by noting the strength of the response.

These assays may be conducted directly as described above or competitively with known toxins. For example, one approach might be to measure the diminution in binding of labeled BT cry toxin in the presence and absence of the toxin candidate.

In addition to simply screening candidates, the screen can be used to devise improved forms of toxins which are more specific or less specific to particular classes of insects as desired. The ability to determine binding affinity ($K_a$ and $K_d$), dissociation and association rates, and cytotoxic effects of a candidate allows quick, accurate and reproducible screening techniques for a large number of toxins and other ligands under identical conditions which was not possible heretofore. Such information will facilitate the selection of the most effective toxins and ligands for any given receptor obtained from any desired host cell.

Competition assays may also employ antibodies that are specifically immunoreactive with the receptor. Such antibodies can be prepared in the conventional manner by administering the purified receptor to a vertebrate animal, monitoring antibody titers and recovering the antisera or the antibody-producing cells for immortalization, to obtain immortalized cells capable of secreting antibodies of the appropriate specificity. Techniques for obtaining immortalized B cells and for screening them for secretion of the desired antibody are now conventional in the art. The resulting monoclonal antibodies may be more effective than the polyclonal antisera as competition reagents; furthermore, the availability of the immortalized cell line secreting the desired antibody assures uniformity of production of the same reagent over time. The information and the structural characteristics of toxins and ligands tested will permit a rational approach to designing more efficient toxins and ligands. Additionally, such assays will lead to a better understanding of the function and the structure/function relationship of both toxin/ligand and BT-$R_1$ analogs. In turn, this will allow the development of highly effective toxins/ligands. Ligands include natural and modified toxins, antibodies (anti-receptor and antiidiotypic antibodies which mimic a portion of a toxin that binds to a receptor, and whatever small molecules bind the receptors.

Therapeutic Strategies

Advantage may be taken of the ability of receptors to mediate the destruction, dissociation or association of cells, tissues or organs by utilizing the screening assay as a method to identify successful therapeutics in the treatment of, for example, malignancies, metastases and infectious microorganisms which naturally express receptors corresponding to BT-$R_1$. The presence of receptors corresponding to the BT-$R_1$ receptor illustrated herein and members of the family of receptors included in the invention in the undesired cells may be exploited by first assessing the interaction of a proposed therapeutic with the receptors on these cells in culture and then identifying agents which successfully interact with the receptors as useful candidate reagents. Antibodies reactive with these receptors comprise a class of promising therapeutic candidates.

In some applications target cells, tissues, organs, and microorganisms which do not express an effective receptor corresponding to the BT-$R_1$ receptor may be transformed or transfected to express an effective corresponding receptor. These targets then will be killed or manipulated with toxin or other ligands. For instance, yeast cells to be used for toxin assays for a particular insect may be transformed with a genetic construct for expression of the receptor from that insect which corresponds to the BT-$R_1$ receptor.

In another aspect of the invention the receptors corresponding to BT-$R_1$ in certain target cells may be manipulated by modified toxin or other ligands to prevent the normal response to toxin (dissociation, damage and death of membranes, cell, tissues and organisms). For instance, a ligand which binds to a corresponding receptor in such a way that normal receptor function is inhibited would thereby prevent the receptor from initiating the usual destructive effects in the presence of a normal ligand such as a toxin. In other words, the invention enables development of competitive inhibitors of a toxin or other ligand which normally initiates destructive or other effects via a receptor corresponding to BT-$R_1$.

The following examples are intended to illustrate but not to limit the invention.

EXAMPLE 1

Purification and Sequence Determination of BT-$R_1$ Protein

Midguts of *M. sexta* were extracted and the BT-$R_1$ protein purified according to the method of Vadlamudi, R. K. et al. *J Biol Chem* (1993) 268:1233, referenced above and incorporated herein by reference. The electroeluted band was confirmed to contain BT-$R_1$ protein by binding to $^{125}$I-cryIA (b) toxin. In gel electrophoresis, the protein bound to toxin had an apparent weight of approximately 210 kD under reducing and nonreducing conditions.

The purified electroeluted BT-$R_1$ was subjected to cyanogen bromide digestion and the. cyanogen bromide fragments separated on a 17% high-resolution tricine SDS-polyacrylamide gel as described by Schagger, H. et al. *Anal Biochem* (1987) 166:368. The separated fragments were transferred to Problott membranes (Applied Biosystems) and five bands were extracted and subjected to microsequencing using standard instrumentation. The amino acid sequences obtained were:

1. (Met)-Leu-Asp-Tyr-Glu-Val-Pro-Glu-Phe-Gln-Ser-Ile-Thr-Ile-Arg-Val-Val-Ala-Thr-Asp-Asn-Asn-Asp-Thr-Arg-His-Val-Gly-Val-Ala (SEQ ID NO:18);

2. (Met)-X-Glu-Thr-Tyr-Glu-Leu-Ile-Ile-His-Pro-Phe-Asn-Tyr-Tyr-Ala (SEQ ID NO:19);

3. (Met)-X-X-X-His-Gln-Leu-Pro-Leu-Ala-Gln-Asp-Ile-Lys-Asn-His (SEQ ID NO:20);

4. (Met)-Phe/Pro-Asn/Ile-Val-Arg/Tyr-Val-Asp-Ile/Gly (SEQ ID NO:21);

5. (Met)-Asn-Phe-Phe/His-Ser-Val-Asn-Arg/Asp-Glu (SEQ ID NO:23).

EXAMPLE 2

Recovery of cDNA

An *M. sexta* cDNA library was constructed from midgut tissue in λgt10 using the Superscript Choice System according to the manufacturer's instructions (Life Technologies, Inc.). Degenerate oligonucleotide probes were constructed based on the peptide sequences determined in Example 1 using the methods and approach described in Zhang, S. et al. *Gene* (1991) 105:61. Synthetic oligonucleotides corresponding to peptides 1–3 of Example 1 were labeled with $\gamma^{32}P$ using polynucleotide kinase and used as probes as described in the standard cloning manual of Maniatis, T. et al. *Molecular Cloning: A Laboratory Manual* (Cold Spring Harbor Laboratory, Cold Spring Harbor, N.Y., 2nd ed. 1989). A clone hybridizing to all three probes identified from 40 positive clones as hybridizing to all three of the probes was plaque-purified from a screen of $4\times10^5$ recombinants and subcloned into pBluescript (Stratagene). It contained an insert of 5571 bp.

Figure 1A:
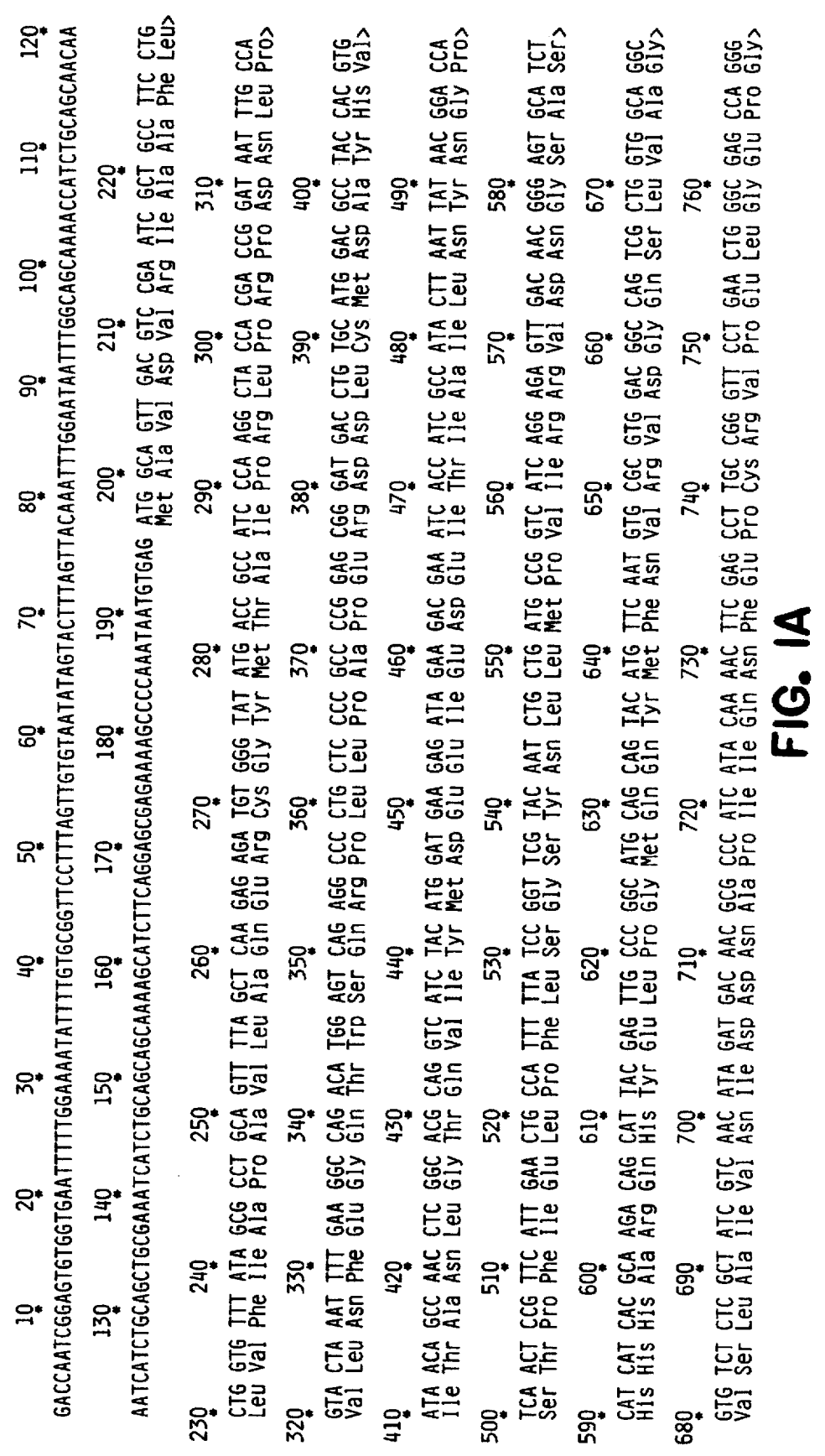

Double-stranded cDNA in pBluescript was sequenced in both directions by the dideoxy termination method with Sequanase (USB) according to the manufacturer's instructions. The sequencing showed an open reading frame of 4584 base pairs or 1528 amino acids along with a polyadenylation signal at position 5561. The sequence obtained and the deduced amino acid sequence is shown in FIG. 1A-1F (SEQ ID NOS: 1 and 2).

Thus, the deduced protein has a molecular mass of 172 kD and a pI of approximately 4.5. The amino acid sequences of the cyanogen bromide fragments of native receptor match perfectly within the deduced amino acid sequence. The open reading frame begins with an ATG that is flanked by the consensus translation initiation sequence GAGATGG for eucaryotic mRNAs as described by Kozak, M. *Nucleic Acids Res* (1987) 15:8125.

As shown in FIG. 1, the deduced amino acid sequence includes a putative signal, shown underlined, preceding the mature N-terminus Asn-Glu-Arg-etc. Eleven repeats (cad1–cad11) are shown in the extracellular region upstream of the membrane domain, shown with the heavy underline, at positions 1406–1427. The end of the 11th repeat is shown with an arrowhead. The positions of the five CNBR fragments are also shown under the complete sequence.

Like known cadherins, the external domain of $BT-R_1$ is highly repetitive and contains 11 repeats (cad1–cad11; see FIGS. 2A–2F (SEQ ID NO:2)). The greatest similarity of $BT\text{-}R_1$ to the cadherins is with the extracellular repeats of the cadherin motif of mouse P-cadherin, Drosophila fat tumor suppressor and the protocadherins, although homologies are not high (20–40 homology and 30–60 percent similarity). The conserved repeats of $BT\text{-}R_1$ included AXDXD SEQ ID NO:23), DXE, DXNDXXP (SEQ ID NO:24), one glutamic acid residue and two glycine residues. Motifs A/VXDXD (SEQ ID NO:25), DXNDN (SEQ ID NO:26) are the consensus sequences for calcium binding and two such regions are present in a typical cadherin repeat. In all repeats of $BT\text{-}R_1$, the sequence DXNDN (SEQ ID NO:26) is preceded by 8 to 14 hydrophobic amino acids. Similar hydrophobic sequences also have been observed in the cadherins. The length of the hydrophobic stretches suggests that these areas are not transmembrane regions but that they represent β-sheet structures commonly present in cadherin-like repeats. $BT\text{-}R_1$ contains a putative cytoplasmic domain of 101 amino acids, smaller than vertebrate cadherin cytoplasmic domains (160 amino acids), and shows no homology to any of the cadherin cytoplasmic domains or to cytoplasmic domains of other proteins to which it has been compared in a current sequence data base.

To confirm that the sequenced clone encoded full-length $BT\text{-}R_1$ protein, total mRNA was prepared from midguts of *M. sexta* subjected to Northern blot by hybridization with the antisense 4.8 kb SacI fragment of the $BT\text{-}R_1$ cDNA clone. The Northern blot analysis was conducted by hybridizing to the antisense probe at 42° C. and 50% formamide, 5× Denhardt's Reagent, 5× SSCP and 50 μg/ml salmon sperm DNA. The filter was then washed two times with 1× SSC+0.1% SDS and two times with 0.15× SSC+0.1% SDS at 42° C. Each wash was roughly 20 minutes. The filter was then exposed to X-ray film for 24 hours. The 4.8 kb probe hybridized to a single 5.6 kb band.

The $BT\text{-}R_1$ clone was translated using rabbit reticulolysate and the resulting translated products were immunoprecipitated with antisera raised against native protein encoded by $BT\text{-}R_1$. For the in vitro translation, pBluescript plasmid containing $BT\text{-}R_1$ cDNA was linearized and transcribed with $T_3$ polymerase (Pharmacia). The translation was conducted according to manufacturer's instructions with nuclease-treated rabbit reticulolysate (Life Technologies, Inc.). After one hour of incubation at 30° C., the reaction mixture was combined with an equal volume of SDS buffer or lysed with 50 mM Tris buffer containing 1% NP40 and 250 mM NaCl (pH 8.0) for immunoprecipitation. Preimmune serum was used as a control. Translation and immunoprecipitation products were electrophoresed on a 7.5% SDS-polyacrylamide gel fixed, treated with Enhance (Dupont NEN), dried and exposed to X-ray film for 12 hours.

Two protein bands of approximately 172 kD and 150 kD as determined by SDS-PAGE were obtained; it is postulated that the 150 kD translation product was due to initiation of translation from an internal methionine at amino acid 242. This is consistent with the observations of Kozak, M. *Mol Cell Biol* (1989) 9:5073.

Thus, both results confirm that a full-length clone was obtained.

EXAMPLE 3

Recombinant Production and Characteristics of the $BT\text{-}R_1$ Protein

The $BT\text{-}R_1$ cDNA clone was subcloned into the mammalian expression vector pcDNA3 (Invitrogen) and the construct transfected into COS-7 cells. Membranes isolated from the COS-7 transfectants were solubilized, electrophoresed and ligand blotted with $^{125}$I-cryIA(b) toxin. The cells were harvested 60 hours after transfection, washed with phosphate-buffered saline and lysed by freezing in liquid nitrogen. Cell membranes were prepared by differential centrifugation as described by Elshourbagy, N. A. et al. *J Biol Chem* (1993) 266:3873. Control cells were COS-7 cells transfected with pcDNA3.

The cell membranes (10 μg) were separated on 7.5% SDS-PAGE blotted to a nylon membrane and blocked with Tris-buffered saline containing 5% nonfat dry milk powder, 5% glycerol and 1% Tween-20. The nylon membrane was then incubated with $^{125}$I-cryIA(b) toxin ($2 \times 10^5$ cpm/ml) for two hours with blocking buffer, dried and exposed to X-ray film at −70° C. The labeled toxin bound to a 210±5 kD protein; the 210 kD band was observed only in lanes containing membranes prepared from either *M. sexta* or COS-7 cells transfected with the BT-R$_1$ cDNA construct containing 4810 bp of cDNA comprising the open reading frame.

The discrepancy between the 210 kD protein expressed and the calculated 172 kD molecular weight is due to glycosylation of the protein; in vitro translation of the cDNA clone, as described above, which does not result in glycosylation, does produce the 172 kD protein. To verify this, the COS-7 produced protein was subjected to digestion with N-glycosidase-F by first denaturing the purified protein by boiling in 1% SDS for 5 minutes followed by addition of NP-40 to a final concentration of 1% in the presence of 0.1% SDS, and then incubating the denatured protein in sodium phosphate buffer, pH 8.5 at 37° C. with N-glycosidase-F for 10 hours. Controls were incubated under the same conditions without enzyme. Digestion products were separated on a 7.5% SDS-PAGE and stained with Coomassie brilliant blue. This glycosidase treatment reduced the molecular weight of BT-R$_1$ protein from 210 to 190 kD; this indicates N-glycosylation at some of the 16 consensus N-glycosylation sites in the protein. Treatment of BT-R$_1$ with O-glycosidase and neuraminidase did not alter the mobility of the protein.

In addition, embryonic 293 cells were transfected with the BT-R$_1$ cDNA clone in pcDNA3 and incubated with the labeled toxin (0.32 nM) in the presence of increasing concentrations (0 to $10^6$M) of unlabeled toxin. Nonspecific binding was measured as bound radioactivity in the presence of 1 µM unlabeled toxin. A value for the dissociation constant ($K_d$) of 1015 pM was determined by Scatchard analysis; this is approximately the same value that was obtained for the natural receptor as described by Vadlamudi, R. K. et al. *J Biol Chem* (1993) (supra).

EXAMPLE 4

Physiological Effect of BT Toxin on Modified Embryonic 293 Cells

Both unmodified embryonic 293 cells, and 293 cells which have been modified to produce the BT-R$_1$ receptor as described in Example 3, when cultured in vitro form adherent star-shaped clusters. When BT toxin (200 nM) is added to serum-free medium, tee clusters round up and release from the plastic surfaces of the culture dish. This effect is also observed under known conditions of cytotoxicity for 293 cells. The foregoing effect is observed only when the cells are cultured in serum-free medium since the toxin binds to serum and would thus be ineffective under conditions where serum is present.

However, in the presence of anti-receptor antisera, this effect of BT toxin is blocked. Also, when serum is added back to a culture of modified E293 cells which has been treated in serum-free conditions with the toxin, the cells revert to their normal star-shaped adherent cluster shapes. This indicates that the effect of the toxin is reversible.

We claim:

1. A polynucleotide in purified and isolated form which comprises a nucleotide sequence which encodes a receptor that specifically binds a Bacillus thuringiensis (BT) toxin wherein said receptor has the amino acid sequence of the receptor encoded by the insert in the plasmid pBT-$R_1$ deposited at the American Type Culture Collection as ATCC 98713, or wherein said receptor is a naturally occurring receptor that is encoded by a nucleotide sequence that hybridizes at 40°–50° C. in 1×SSC, or equivalent conditions thereof, to the cDNA insert in the plasmid pBT-$R_1$ deposited at the American Type Culture Collection as ATCC 98713.

2. The polynucleotide of claim 1 wherein said toxin is the cryIA(b) toxin of B. thuringiensis subsp. berliner.

3. The polynucleotide of claim 1 wherein said toxin is a modified form of BT toxin.

4. The polynucleotide of claim 1 wherein said receptor is the BT-$R_1$ receptor of the tobacco hornworm Manduca sexta encoded by the insert in the plasmid pBT-$R_1$ deposited at the American Type Culture Collection as ATCC 98713.

5. A recombinant expression system for expression of a nucleotide sequence encoding a receptor which specifically binds a BT toxin, wherein said receptor has the amino acid sequence of the receptor encoded by the insert in the plasmid pBT-$R_1$ deposited at the American Type Culture Collection as ATCC 98713, or wherein said receptor is a naturally occurring receptor that is encoded by a nucleotide sequence that hybridizes at 40°–50° C. in 1×SSC, or equivalent conditions thereof, to the cDNA insert in the plasmid pBT-$R_1$ deposited at the American Type Culture Collection as ATCC 98713, which expression system comprises said encoding nucleotide sequence operably linked to a promoter and optionally one or more additional control sequences in host cells.

6. Recombinant host cells modified to contain the expression system of claim 5.

7. A method to produce a receptor which binds a BT toxin which method comprises culturing the cells of claim 6 under conditions wherein said receptor is produced; and optionally recovering said receptor from the culture.

8. The method of claim 7 wherein said receptor is disposed at the surface of said cells.

9. The method of claim 8 further comprising a step wherein said cells having said receptor disposed at their surface are recovered from the culture for use in an assay.

10. The method of claim 8 further comprising a step wherein said receptor is recovered from said cells having said receptor disposed at their surface.

11. Cells expressing BT toxin receptor disposed at their surface prepared by the method of claim 9.

12. The cells of claim 11 wherein the receptor is a naturally occurring insect receptor that binds a BT toxin.

13. A receptor produced by the method of claim 7 wherein said receptor binds a BT toxin.

14. An isolated polynucleotide that encodes the BT-$R_1$ receptor of the tobacco hornworm Manduca sexta encoded by the insert in the plasmid pBT-$R_1$ deposited at the American Type Culture Collection as ATCC 98713.

15. The polynucleotide of claim 14 wherein said polynucleotide has the nucleotide sequence of the insert of the plasmid deposited at the American Type Culture Collection as ATCC 98713.

16. A purified and isolated polynucleotide which comprises a nucleotide sequence complementary to a nucleotide sequence encoding a receptor which binds to BT toxin wherein said receptor has the amino acid sequence of the receptor encoded by the insert in the plasmid pBT-$R_1$ deposited at the American Type Culture Collection as ATCC 98713, or wherein said receptor is a naturally occurring receptor that is encoded by a nucleotide sequence that hybridizes at 40°–50° C. in 1×SSC, or equivalent conditions thereof, to the cDNA insert in the plasmid pBT-$R_1$ deposited at the American Type Culture Collection as ATCC 98713.

* * * * *

UNITED STATES PATENT AND TRADEMARK OFFICE
CERTIFICATE OF CORRECTION

PATENT NO. : 5,693,491 Page 1 of 1
DATED : December 2, 1997
INVENTOR(S) : Lee A. Bulla It is certified that error appears in the above-identified patent and that said Letters Patent is hereby corrected as shown below:

Column 3,
Line 15, delete "98713" and substitute therefor -- 98173 --.
Line 47, delete "98713" and substitute therefor -- 98173 --.

Claim 1,
Line 20, delete "98713" and substitute therefor -- 98173 --.
Line 24, delete "98713" and substitute therefor -- 98173 --.

Claim 4,
Line 32, delete "98713" and substitute therefor -- 98173 --.

Claim 5,
Line 38, delete "98713" and substitute therefor -- 98173 --.
Line 43, delete "98713" and substitute therefor -- 98173 --.

Claim 14,
Line 33, delete "98713" and substitute therefor -- 98173 --.

Claim 15,
Line 37, delete "98713" and substitute therefor -- 98173 --.

Claim 16,
Line 44, delete "98713" and substitute therefor -- 98173 --.
Line 48, delete "98713" and substitute therefor -- 98173 --.

Signed and Sealed this

Seventh Day of August, 2001

*Attest:*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 5577 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 197..4780

( x i ) SEQUENCE DESCRIPTION: SEQ ID NO:1:

```
GACCAATCGG AGTGTGGTGA ATTTTTGGAA AATATTTTGT GCGGTTCCTT TAGTTGTGTA        60

ATATAGTACT TTAGTTACAA ATTTGGAATA ATTTGGCAGC AAAACCATCT GCAGCAACAA       120

AATCATCTGC AGCTGCGAAA TCATCTGCAG CAGCAAAAGC ATCTTCAGGA GCGAGAAAAG       180

CCCCAAATAA TGTGAG ATG GCA GTT GAC GTC CGA ATC GCT GCC TTC CTG          229
                Met Ala Val Asp Val Arg Ile Ala Ala Phe Leu
                  1               5                  10

CTG GTG TTT ATA GCG CCT GCA GTT TTA GCT CAA GAG AGA TGT GGG TAT         277
Leu Val Phe Ile Ala Pro Ala Val Leu Ala Gln Glu Arg Cys Gly Tyr
              15                  20                  25

ATG ACC GCC ATC CCA AGG CTA CCA CGA CCG GAT AAT TTG CCA GTA CTA         325
Met Thr Ala Ile Pro Arg Leu Pro Arg Pro Asp Asn Leu Pro Val Leu
          30                  35                  40
```

```
AAT TTT GAA GGC CAG ACA TGG AGT CAG AGG CCC CTG CTC CCC GCC CCG      373
Asn Phe Glu Gly Gln Thr Trp Ser Gln Arg Pro Leu Leu Pro Ala Pro
    45                      50                  55

GAG CGG GAT GAC CTG TGC ATG GAC GCC TAC CAC GTG ATA ACA GCC AAC      421
Glu Arg Asp Asp Leu Cys Met Asp Ala Tyr His Val Ile Thr Ala Asn
60                      65                  70                  75

CTC GGC ACG CAG GTC ATC TAC ATG GAT GAA GAG ATA GAA GAC GAA ATC      469
Leu Gly Thr Gln Val Ile Tyr Met Asp Glu Glu Ile Glu Asp Glu Ile
                80                      85                  90

ACC ATC GCC ATA CTT AAT TAT AAC GGA CCA TCA ACT CCG TTC ATT GAA      517
Thr Ile Ala Ile Leu Asn Tyr Asn Gly Pro Ser Thr Pro Phe Ile Glu
            95                      100                 105

CTG CCA TTT TTA TCC GGT TCG TAC AAT CTG CTG ATG CCG GTC ATC AGG      565
Leu Pro Phe Leu Ser Gly Ser Tyr Asn Leu Leu Met Pro Val Ile Arg
        110                     115                 120

AGA GTT GAC AAC GGG AGT GCA TCT CAT CAT CAC GCA AGA CAG CAT TAC      613
Arg Val Asp Asn Gly Ser Ala Ser His His His Ala Arg Gln His Tyr
    125                     130                     135

GAG TTG CCC GGC ATG CAG CAG TAC ATG TTC AAT GTG CGC GTG GAC GGC      661
Glu Leu Pro Gly Met Gln Gln Tyr Met Phe Asn Val Arg Val Asp Gly
140                     145                     150                 155

CAG TCG CTG GTG GCA GGC GTG TCT CTC GCT ATC GTC AAC ATA GAT GAC      709
Gln Ser Leu Val Ala Gly Val Ser Leu Ala Ile Val Asn Ile Asp Asp
                160                     165                     170

AAC GCG CCC ATC ATA CAA AAC TTC GAG CCT TGC CGG GTT CCT GAA CTG      757
Asn Ala Pro Ile Ile Gln Asn Phe Glu Pro Cys Arg Val Pro Glu Leu
            175                     180                     185

GGC GAG CCA GGG TTG ACA GAA TGC ACA TAC CAA GTA TCG GAC GCG GAC      805
Gly Glu Pro Gly Leu Thr Glu Cys Thr Tyr Gln Val Ser Asp Ala Asp
        190                     195                     200

GGA CGG ATC AGC ACA GAG TTC ATG ACG TTC AGG ATC GAC AGC GTT CGT      853
Gly Arg Ile Ser Thr Glu Phe Met Thr Phe Arg Ile Asp Ser Val Arg
    205                     210                     215

GGC GAC GAG GAG ACC TTC TAC ATC GAA CGG ACG AAT ATC CCC AAC CAA      901
Gly Asp Glu Glu Thr Phe Tyr Ile Glu Arg Thr Asn Ile Pro Asn Gln
220                     225                     230                 235

TGG ATG TGG CTA AAT ATG ACC ATA GGC GTT AAT ACC TCG CTC AAC TTC      949
Trp Met Trp Leu Asn Met Thr Ile Gly Val Asn Thr Ser Leu Asn Phe
                240                     245                     250

GTC ACC AGT CCG CTG CAT ATA TTC AGC GTG ACA GCC CTG GAC TCG CTC      997
Val Thr Ser Pro Leu His Ile Phe Ser Val Thr Ala Leu Asp Ser Leu
            255                     260                     265

CCG AAC ACC CAC ACG GTG ACT ATG ATG GTG CAA GTG GCG AAT GTG AAC      1045
Pro Asn Thr His Thr Val Thr Met Met Val Gln Val Ala Asn Val Asn
        270                     275                     280

AGC CGT CCG CCG CGC TGG CTG GAG ATC TTC GCT GTC CAA CAG TTT GAA      1093
Ser Arg Pro Pro Arg Trp Leu Glu Ile Phe Ala Val Gln Gln Phe Glu
    285                     290                     295

GAG AAA TCT TAC CAA AAC TTC ACA GTG AGG GCG ATC GAC GGA GAC ACT      1141
Glu Lys Ser Tyr Gln Asn Phe Thr Val Arg Ala Ile Asp Gly Asp Thr
300                     305                     310                 315

GAG ATC AAT ATG CCT ATC AAC TAC AGG CTG ATC ACA AAT GAG GAA GAC      1189
Glu Ile Asn Met Pro Ile Asn Tyr Arg Leu Ile Thr Asn Glu Glu Asp
                320                     325                     330

ACA TTC TTC AGC ATT GAG GCC CTG CCT GGT GGA AAA AGC GGG GCT GTA      1237
Thr Phe Phe Ser Ile Glu Ala Leu Pro Gly Gly Lys Ser Gly Ala Val
            335                     340                     345

TTC CTC GTG TCG CCA ATT GAC CGC GAC ACA CTG CAA CGA GAG GTG TTT      1285
Phe Leu Val Ser Pro Ile Asp Arg Asp Thr Leu Gln Arg Glu Val Phe
        350                     355                     360
```

-continued

| | | | | | | | | | | | | | | | | |
|---|---|---|---|---|---|---|---|---|---|---|---|---|---|---|---|---|
| CCA | CTT | ACG | ATC | GTC | GCT | TAC | AAA | TAT | GAT | GAG | GAG | GCC | TTC | TCC | ACA | 1333 |
| Pro | Leu | Thr | Ile | Val | Ala | Tyr | Lys | Tyr | Asp | Glu | Glu | Ala | Phe | Ser | Thr | |
| | 365 | | | | | 370 | | | | | 375 | | | | | |
| TCA | ACA | AAC | GTG | GTC | ATC | ATT | GTG | ACA | GAC | ATC | AAC | GAC | CAA | AGA | CCT | 1381 |
| Ser | Thr | Asn | Val | Val | Ile | Ile | Val | Thr | Asp | Ile | Asn | Asp | Gln | Arg | Pro | |
| 380 | | | | | 385 | | | | | 390 | | | | | 395 | |
| GAA | CCT | ATA | CAC | AAG | GAA | TAT | CGA | CTG | GCA | ATC | ATG | GAG | GAG | ACG | CCC | 1429 |
| Glu | Pro | Ile | His | Lys | Glu | Tyr | Arg | Leu | Ala | Ile | Met | Glu | Glu | Thr | Pro | |
| | | | | 400 | | | | | 405 | | | | | 410 | | |
| CTG | ACC | CTC | AAC | TTC | GAT | AAA | GAA | TTC | GGA | TTT | CAT | GAT | AAG | GAT | TTA | 1477 |
| Leu | Thr | Leu | Asn | Phe | Asp | Lys | Glu | Phe | Gly | Phe | His | Asp | Lys | Asp | Leu | |
| | | | 415 | | | | | 420 | | | | | 425 | | | |
| GGT | CAA | AAC | GCT | CAG | TAC | ACG | GTG | CGT | CTA | GAG | AGC | GTG | GAC | CCT | CCA | 1525 |
| Gly | Gln | Asn | Ala | Gln | Tyr | Thr | Val | Arg | Leu | Glu | Ser | Val | Asp | Pro | Pro | |
| | | 430 | | | | | 435 | | | | | 440 | | | | |
| GGC | GCT | GCT | GAG | GCA | TTC | TAC | ATA | GCG | CCT | GAA | GTC | GGC | TAC | CAG | CGA | 1573 |
| Gly | Ala | Ala | Glu | Ala | Phe | Tyr | Ile | Ala | Pro | Glu | Val | Gly | Tyr | Gln | Arg | |
| | 445 | | | | | 450 | | | | | 455 | | | | | |
| CAG | ACC | TTC | ATC | ATG | GGC | ACC | CTC | AAT | CAC | TCC | ATG | CTG | GAT | TAC | GAA | 1621 |
| Gln | Thr | Phe | Ile | Met | Gly | Thr | Leu | Asn | His | Ser | Met | Leu | Asp | Tyr | Glu | |
| 460 | | | | | 465 | | | | | 470 | | | | | 475 | |
| GTG | CCA | GAG | TTT | CAG | AGT | ATT | ACG | ATT | CGG | GTG | GTA | GCG | ACC | GAC | AAC | 1669 |
| Val | Pro | Glu | Phe | Gln | Ser | Ile | Thr | Ile | Arg | Val | Val | Ala | Thr | Asp | Asn | |
| | | | | 480 | | | | | 485 | | | | | 490 | | |
| AAC | GAC | ACG | AGG | CAC | GTG | GGC | GTC | GCG | TTG | GTT | CAC | ATT | GAC | CTC | ATC | 1717 |
| Asn | Asp | Thr | Arg | His | Val | Gly | Val | Ala | Leu | Val | His | Ile | Asp | Leu | Ile | |
| | | | 495 | | | | | 500 | | | | | 505 | | | |
| AAT | TGG | AAC | GAT | GAG | CAG | CCG | ATC | TTC | GAA | CAC | GCC | GTG | CAG | ACC | GTC | 1765 |
| Asn | Trp | Asn | Asp | Glu | Gln | Pro | Ile | Phe | Glu | His | Ala | Val | Gln | Thr | Val | |
| | | 510 | | | | | 515 | | | | | 520 | | | | |
| ACC | TTC | GAC | GAG | ACT | GAA | GGC | GAG | GGG | TTC | TTC | GTC | GCC | AAG | GCG | GTT | 1813 |
| Thr | Phe | Asp | Glu | Thr | Glu | Gly | Glu | Gly | Phe | Phe | Val | Ala | Lys | Ala | Val | |
| | 525 | | | | | 530 | | | | | 535 | | | | | |
| GCA | CAC | GAC | AGA | GAC | ATC | GGG | GAT | GTC | GTC | GAG | CAT | ACT | TTA | TTG | GGT | 1861 |
| Ala | His | Asp | Arg | Asp | Ile | Gly | Asp | Val | Val | Glu | His | Thr | Leu | Leu | Gly | |
| 540 | | | | | 545 | | | | | 550 | | | | | 555 | |
| AAC | GCT | GTT | AAC | TTC | CTG | ACC | ATC | GAC | AAA | CTC | ACC | GGC | GAC | ATC | CGC | 1909 |
| Asn | Ala | Val | Asn | Phe | Leu | Thr | Ile | Asp | Lys | Leu | Thr | Gly | Asp | Ile | Arg | |
| | | | | 560 | | | | | 565 | | | | | 570 | | |
| GTC | TCA | GCT | AAC | GAC | TCC | TTC | AAC | TAC | CAT | CGA | GAA | AGT | GAA | TTA | TTT | 1957 |
| Val | Ser | Ala | Asn | Asp | Ser | Phe | Asn | Tyr | His | Arg | Glu | Ser | Glu | Leu | Phe | |
| | | | 575 | | | | | 580 | | | | | 585 | | | |
| GTG | CAG | GTG | CGA | GCT | ACA | GAC | ACG | CTG | GGC | GAA | CCC | TTC | CAC | ACG | GCG | 2005 |
| Val | Gln | Val | Arg | Ala | Thr | Asp | Thr | Leu | Gly | Glu | Pro | Phe | His | Thr | Ala | |
| | | 590 | | | | | 595 | | | | | 600 | | | | |
| ACG | TCA | CAG | CTG | GTC | ATA | CGA | CTA | AAT | GAC | ATC | AAC | AAC | ACG | CCA | CCC | 2053 |
| Thr | Ser | Gln | Leu | Val | Ile | Arg | Leu | Asn | Asp | Ile | Asn | Asn | Thr | Pro | Pro | |
| | 605 | | | | | 610 | | | | | 615 | | | | | |
| ACC | TTA | CGG | CTG | CCT | CGA | GGC | AGT | CCC | CAA | GTG | GAG | GAG | AAC | GTG | CCT | 2101 |
| Thr | Leu | Arg | Leu | Pro | Arg | Gly | Ser | Pro | Gln | Val | Glu | Glu | Asn | Val | Pro | |
| 620 | | | | | 625 | | | | | 630 | | | | | 635 | |
| GAT | GGC | CAC | GTC | ATC | ACC | CAG | GAG | TTA | CGC | GCC | ACC | GAC | CCC | GAC | ACC | 2149 |
| Asp | Gly | His | Val | Ile | Thr | Gln | Glu | Leu | Arg | Ala | Thr | Asp | Pro | Asp | Thr | |
| | | | | 640 | | | | | 645 | | | | | 650 | | |
| ACG | GCC | GAT | CTG | CGC | TTC | GAG | ATA | AAC | TGG | GAC | ACC | TCT | TTC | GCC | ACC | 2197 |
| Thr | Ala | Asp | Leu | Arg | Phe | Glu | Ile | Asn | Trp | Asp | Thr | Ser | Phe | Ala | Thr | |
| | | | 655 | | | | | 660 | | | | | 665 | | | |
| AAG | CAA | GGC | CGC | CAG | GCT | AAC | CCC | GAC | GAG | TTT | AGG | AAT | TGC | GTG | GAA | 2245 |
| Lys | Gln | Gly | Arg | Gln | Ala | Asn | Pro | Asp | Glu | Phe | Arg | Asn | Cys | Val | Glu | |
| | | 670 | | | | | 675 | | | | | 680 | | | | |

-continued

| | | | | | | | | | | | | | | | | |
|---|---|---|---|---|---|---|---|---|---|---|---|---|---|---|---|---|
| ATC | GAG | ACC | ATC | TTC | CCC | GAG | ATT | AAC | AAC | CGG | GGA | CTG | GCT | ATC | GGC | 2293 |
| Ile | Glu | Thr | Ile | Phe | Pro | Glu | Ile | Asn | Asn | Arg | Gly | Leu | Ala | Ile | Gly | |
| | 685 | | | | 690 | | | | | 695 | | | | | | |
| CGC | GTT | GTA | GCG | CGC | GAA | ATC | AGA | CAC | AAC | GTG | ACC | ATA | GAC | TAC | GAG | 2341 |
| Arg | Val | Val | Ala | Arg | Glu | Ile | Arg | His | Asn | Val | Thr | Ile | Asp | Tyr | Glu | |
| 700 | | | | | 705 | | | | | 710 | | | | | 715 | |
| GAG | TTT | GAG | GTC | CTC | TCC | CTC | ACA | GTG | AGG | GTG | CGT | GAC | CTT | AAC | ACC | 2389 |
| Glu | Phe | Glu | Val | Leu | Ser | Leu | Thr | Val | Arg | Val | Arg | Asp | Leu | Asn | Thr | |
| | | | | 720 | | | | | 725 | | | | | 730 | | |
| GTC | TAC | GGA | GAC | GAC | TAC | GAC | GAA | TCG | ATG | CTC | ACA | ATA | ACT | ATA | ATC | 2437 |
| Val | Tyr | Gly | Asp | Asp | Tyr | Asp | Glu | Ser | Met | Leu | Thr | Ile | Thr | Ile | Ile | |
| | | | 735 | | | | | 740 | | | | | 745 | | | |
| GAT | ATG | AAC | GAC | AAC | GCG | CCG | GTG | TGG | GTG | GAG | GGG | ACT | CTG | GAG | CAG | 2485 |
| Asp | Met | Asn | Asp | Asn | Ala | Pro | Val | Trp | Val | Glu | Gly | Thr | Leu | Glu | Gln | |
| | | 750 | | | | | 755 | | | | | 760 | | | | |
| AAC | TTC | CGA | GTC | CGC | GAG | ATG | TCG | GCG | GGC | GGG | CTC | GTG | GTG | GGC | TCC | 2533 |
| Asn | Phe | Arg | Val | Arg | Glu | Met | Ser | Ala | Gly | Gly | Leu | Val | Val | Gly | Ser | |
| | 765 | | | | | 770 | | | | | 775 | | | | | |
| GTG | CGC | GCG | GAC | GAC | ATC | GAC | GGA | CCG | CTC | TAC | AAC | CAA | GTG | CGA | TAC | 2581 |
| Val | Arg | Ala | Asp | Asp | Ile | Asp | Gly | Pro | Leu | Tyr | Asn | Gln | Val | Arg | Tyr | |
| 780 | | | | | 785 | | | | | 790 | | | | | 795 | |
| ACC | ATT | TTC | CCT | CGT | GAA | GAC | ACA | GAT | AAG | GAC | CTG | ATA | ATG | ATC | GAC | 2629 |
| Thr | Ile | Phe | Pro | Arg | Glu | Asp | Thr | Asp | Lys | Asp | Leu | Ile | Met | Ile | Asp | |
| | | | | 800 | | | | | 805 | | | | | 810 | | |
| TTC | CTC | ACG | GGT | CAA | ATT | TCC | GTG | AAC | ACA | AGC | GGC | GCC | ATC | GAC | GCG | 2677 |
| Phe | Leu | Thr | Gly | Gln | Ile | Ser | Val | Asn | Thr | Ser | Gly | Ala | Ile | Asp | Ala | |
| | | | 815 | | | | | 820 | | | | | 825 | | | |
| GAT | ACT | CCT | CCA | CGC | TTC | CAC | CTC | TAC | TAT | ACA | GTG | GTC | GCT | AGT | GAC | 2725 |
| Asp | Thr | Pro | Pro | Arg | Phe | His | Leu | Tyr | Tyr | Thr | Val | Val | Ala | Ser | Asp | |
| | | 830 | | | | | 835 | | | | | 840 | | | | |
| CGA | TGC | TCG | ACA | GAA | GAT | CCT | GCA | GAT | TGC | CCC | CCT | GAC | CCG | ACT | TAT | 2773 |
| Arg | Cys | Ser | Thr | Glu | Asp | Pro | Ala | Asp | Cys | Pro | Pro | Asp | Pro | Thr | Tyr | |
| | 845 | | | | | 850 | | | | | 855 | | | | | |
| TGG | GAA | ACC | GAA | GGA | AAT | ATC | ACA | ATC | CAC | ATC | ACC | GAC | ACG | AAC | AAC | 2821 |
| Trp | Glu | Thr | Glu | Gly | Asn | Ile | Thr | Ile | His | Ile | Thr | Asp | Thr | Asn | Asn | |
| 860 | | | | | 865 | | | | | 870 | | | | | 875 | |
| AAG | GTC | CCG | CAG | GCG | GAA | ACG | ACT | AAG | TTC | GAT | ACC | GTC | GTG | TAT | ATT | 2869 |
| Lys | Val | Pro | Gln | Ala | Glu | Thr | Thr | Lys | Phe | Asp | Thr | Val | Val | Tyr | Ile | |
| | | | | 880 | | | | | 885 | | | | | 890 | | |
| TAC | GAG | AAC | GCA | ACC | CAC | TTA | GAC | GAG | GTG | GTC | ACT | CTG | ATA | GCC | AGT | 2917 |
| Tyr | Glu | Asn | Ala | Thr | His | Leu | Asp | Glu | Val | Val | Thr | Leu | Ile | Ala | Ser | |
| | | | 895 | | | | | 900 | | | | | 905 | | | |
| GAT | CTT | GAC | AGA | GAC | GAA | ATA | TAC | CAC | ACG | GTG | AGC | TAC | GTC | ATC | AAT | 2965 |
| Asp | Leu | Asp | Arg | Asp | Glu | Ile | Tyr | His | Thr | Val | Ser | Tyr | Val | Ile | Asn | |
| | | 910 | | | | | 915 | | | | | 920 | | | | |
| TAT | GCA | GTG | AAC | CCT | CGA | CTG | ATG | AAC | TTC | TTC | TCC | GTG | AAC | CGA | GAG | 3013 |
| Tyr | Ala | Val | Asn | Pro | Arg | Leu | Met | Asn | Phe | Phe | Ser | Val | Asn | Arg | Glu | |
| | 925 | | | | | 930 | | | | | 935 | | | | | |
| ACC | GGC | CTG | GTG | TAC | GTG | GAC | TAT | GAG | ACC | CAG | GGT | AGT | GGC | GAG | GTG | 3061 |
| Thr | Gly | Leu | Val | Tyr | Val | Asp | Tyr | Glu | Thr | Gln | Gly | Ser | Gly | Glu | Val | |
| 940 | | | | | 945 | | | | | 950 | | | | | 955 | |
| CTG | GAC | CGT | GAT | GGT | GAT | GAA | CCA | ACG | CAC | CGT | ATC | TTC | TTC | AAC | CTC | 3109 |
| Leu | Asp | Arg | Asp | Gly | Asp | Glu | Pro | Thr | His | Arg | Ile | Phe | Phe | Asn | Leu | |
| | | | | 960 | | | | | 965 | | | | | 970 | | |
| ATC | GAC | AAC | TTC | ATG | GGG | GAA | GGA | GAA | GGT | AAC | AGA | AAT | CAG | AAC | GAC | 3157 |
| Ile | Asp | Asn | Phe | Met | Gly | Glu | Gly | Glu | Gly | Asn | Arg | Asn | Gln | Asn | Asp | |
| | | | 975 | | | | | 980 | | | | | 985 | | | |
| ACA | GAA | GTT | CTC | GTT | ATC | TTG | TTG | GAT | GTG | AAT | GAC | AAT | GCT | CCT | GAA | 3205 |
| Thr | Glu | Val | Leu | Val | Ile | Leu | Leu | Asp | Val | Asn | Asp | Asn | Ala | Pro | Glu | |
| | | 990 | | | | | 995 | | | | | 1000 | | | | |

```
TTG CCA CCG CCG AGC GAA CTC TCT TGG ACT ATA TCT GAG AAC CTT AAG          3253
Leu Pro Pro Pro Ser Glu Leu Ser Trp Thr Ile Ser Glu Asn Leu Lys
    1005                1010                1015

CAG GGC GTC CGT CTT GAA CCA CAT ATC TTC GCC CCG GAC CGC GAC GAG          3301
Gln Gly Val Arg Leu Glu Pro His Ile Phe Ala Pro Asp Arg Asp Glu
1020                1025                1030                1035

CCC GAC ACA GAC AAC TCC AGG GTC GGC TAC GAG ATC CTG AAC CTC AGC          3349
Pro Asp Thr Asp Asn Ser Arg Val Gly Tyr Glu Ile Leu Asn Leu Ser
                1040                1045                1050

ACG GAG CGG GAC ATC GAA GTG CCG GAG CTG TTT GTG ATG ATA CAG ATC          3397
Thr Glu Arg Asp Ile Glu Val Pro Glu Leu Phe Val Met Ile Gln Ile
            1055                1060                1065

GCG AAC GTC ACG GGA GAG CTG GAG ACC GCC ATG GAC CTC AAG GGA TAT          3445
Ala Asn Val Thr Gly Glu Leu Glu Thr Ala Met Asp Leu Lys Gly Tyr
        1070                1075                1080

TGG GGG ACG TAC GCT ATA CAT ATA CGG GCA TTC GAC CAC GGC ATT CCG          3493
Trp Gly Thr Tyr Ala Ile His Ile Arg Ala Phe Asp His Gly Ile Pro
    1085                1090                1095

CAA ATG TCC ATG AAC GAG ACA TAT GAG CTG ATC ATC CAT CCG TTC AAC          3541
Gln Met Ser Met Asn Glu Thr Tyr Glu Leu Ile Ile His Pro Phe Asn
1100                1105                1110                1115

TAC TAC GCG CCT GAG TTC GTC TTC CCG ACC AAC GAT GCC GTC ATA CGA          3589
Tyr Tyr Ala Pro Glu Phe Val Phe Pro Thr Asn Asp Ala Val Ile Arg
                1120                1125                1130

CTT GCG AGG GAA CGA GCT GTA ATC AAT GGA GTT CTA GCG ACA GTG AAC          3637
Leu Ala Arg Glu Arg Ala Val Ile Asn Gly Val Leu Ala Thr Val Asn
            1135                1140                1145

GGA GAG TTC TTG GAG CGG ATA TCG GCG ACT GAT CCG GAC GGA CTC CAC          3685
Gly Glu Phe Leu Glu Arg Ile Ser Ala Thr Asp Pro Asp Gly Leu His
        1150                1155                1160

GCG GGC GTC GTC ACC TTC CAA GTG GTA GGC GAT GAG GAA TCA CAA CGG          3733
Ala Gly Val Val Thr Phe Gln Val Val Gly Asp Glu Glu Ser Gln Arg
    1165                1170                1175

TAC TTT CAA GTA GTT AAC GAT GGC GAG AAC CTC GGC TCG TTG AGG TTA          3781
Tyr Phe Gln Val Val Asn Asp Gly Glu Asn Leu Gly Ser Leu Arg Leu
1180                1185                1190                1195

CTG CAA GCC GTT CCA GAG GAG ATC AGG GAG TTC CGG ATA ACG ATT CGC          3829
Leu Gln Ala Val Pro Glu Glu Ile Arg Glu Phe Arg Ile Thr Ile Arg
                1200                1205                1210

GCT ACA GAC CAG GGA ACG GAC CCA GGA CCG CTG TCC ACG GAC ATG ACG          3877
Ala Thr Asp Gln Gly Thr Asp Pro Gly Pro Leu Ser Thr Asp Met Thr
            1215                1220                1225

TTC AGA GTT GTT TTT GTG CCC ACG CAA GGA GAA CCT AGA TTC GCG TCC          3925
Phe Arg Val Val Phe Val Pro Thr Gln Gly Glu Pro Arg Phe Ala Ser
        1230                1235                1240

TCA GAA CAT GCT GTC GCT TTC ATA GAA AAG AGT GCC GGC ATG GAA GAG          3973
Ser Glu His Ala Val Ala Phe Ile Glu Lys Ser Ala Gly Met Glu Glu
    1245                1250                1255

TCT CAC CAA CTT CCT CTA GCA CAA GAC ATC AAG AAC CAT CTC TGT GAA          4021
Ser His Gln Leu Pro Leu Ala Gln Asp Ile Lys Asn His Leu Cys Glu
1260                1265                1270                1275

GAC GAC TGT CAC AGC ATT TAC TAT CGT ATT ATC GAT GGC AAC AGC GAA          4069
Asp Asp Cys His Ser Ile Tyr Tyr Arg Ile Ile Asp Gly Asn Ser Glu
                1280                1285                1290

GGT CAT TTC GGC CTG GAT CCT GTT CGC AAC AGG TTG TTC CTG AAG AAA          4117
Gly His Phe Gly Leu Asp Pro Val Arg Asn Arg Leu Phe Leu Lys Lys
            1295                1300                1305

GAG CTG ATA AGG GAA CAA AGT GCC TCC CAC ACT CTG CAA GTG GCG GCT          4165
Glu Leu Ile Arg Glu Gln Ser Ala Ser His Thr Leu Gln Val Ala Ala
        1310                1315                1320
```

| | | | | | | | | | | | | | | | | |
|---|---|---|---|---|---|---|---|---|---|---|---|---|---|---|---|---|
| AGT | AAC | TCG | CCC | GAT | GGT | GGC | ATT | CCA | CTT | CCT | GCT | TCC | ATC | CTT | ACT | 4213 |
| Ser | Asn | Ser | Pro | Asp | Gly | Gly | Ile | Pro | Leu | Pro | Ala | Ser | Ile | Leu | Thr | |
| 1325 | | | | 1330 | | | | | | 1335 | | | | | | |
| GTC | ACT | GTT | ACC | GTG | AGG | GAG | GCA | GAC | CCT | CGT | CCA | GTG | TTT | GTG | AGG | 4261 |
| Val | Thr | Val | Thr | Val | Arg | Glu | Ala | Asp | Pro | Arg | Pro | Val | Phe | Val | Arg | |
| 1340 | | | | 1345 | | | | | 1350 | | | | | 1355 | | |
| GAA | TTG | TAC | ACC | GCA | GGG | ATA | TCC | ACA | GCG | GAC | TCC | ATC | GGC | AGA | GAG | 4309 |
| Glu | Leu | Tyr | Thr | Ala | Gly | Ile | Ser | Thr | Ala | Asp | Ser | Ile | Gly | Arg | Glu | |
| | | | | | 1360 | | | | 1365 | | | | | 1370 | | |
| CTG | CTC | AGA | TTA | CAT | GCG | ACC | CAG | TCT | GAA | GGC | TCG | GCC | ATT | ACT | TAT | 4357 |
| Leu | Leu | Arg | Leu | His | Ala | Thr | Gln | Ser | Glu | Gly | Ser | Ala | Ile | Thr | Tyr | |
| | | | 1375 | | | | 1380 | | | | | 1385 | | | | |
| GCT | ATA | GAC | TAC | GAT | ACA | ATG | GTA | GTG | GAC | CCC | AGC | CTG | GAG | GCA | GTG | 4405 |
| Ala | Ile | Asp | Tyr | Asp | Thr | Met | Val | Val | Asp | Pro | Ser | Leu | Glu | Ala | Val | |
| | | | 1390 | | | | 1395 | | | | | 1400 | | | | |
| AGA | CAG | TCG | GCT | TTC | GTA | CTG | AAC | GCT | CAA | ACC | GGA | GTG | CTG | ACG | CTT | 4453 |
| Arg | Gln | Ser | Ala | Phe | Val | Leu | Asn | Ala | Gln | Thr | Gly | Val | Leu | Thr | Leu | |
| | 1405 | | | | | 1410 | | | | | 1415 | | | | | |
| AAT | ATC | CAG | CCC | ACG | GCC | ACG | ATG | CAT | GGA | CTG | TTC | AAA | TTC | GAA | GTC | 4501 |
| Asn | Ile | Gln | Pro | Thr | Ala | Thr | Met | His | Gly | Leu | Phe | Lys | Phe | Glu | Val | |
| 1420 | | | | 1425 | | | | | | 1430 | | | | | 1435 | |
| ACA | GCT | ACT | GAC | ACG | GCC | GGC | GCT | CAG | GAC | CGC | ACC | GAC | GTC | ACC | GTG | 4549 |
| Thr | Ala | Thr | Asp | Thr | Ala | Gly | Ala | Gln | Asp | Arg | Thr | Asp | Val | Thr | Val | |
| | | | 1440 | | | | | 1445 | | | | | 1450 | | | |
| TAC | GTG | GTA | TCC | TCG | CAG | AAC | CGC | GTC | TAC | TTC | GTG | TTC | GTC | AAC | ACG | 4597 |
| Tyr | Val | Val | Ser | Ser | Gln | Asn | Arg | Val | Tyr | Phe | Val | Phe | Val | Asn | Thr | |
| | | | 1455 | | | | | 1460 | | | | | 1465 | | | |
| CTG | CAA | CAG | GTC | GAA | GAC | AAC | AGA | GAC | TTT | ATC | GCG | GAC | ACC | TTC | AGC | 4645 |
| Leu | Gln | Gln | Val | Glu | Asp | Asn | Arg | Asp | Phe | Ile | Ala | Asp | Thr | Phe | Ser | |
| | | 1470 | | | | | 1475 | | | | | 1480 | | | | |
| GCT | GGG | TTC | AAC | ATG | ACC | TGC | AAC | ATC | GAC | CAA | GTG | GTG | CCC | GCT | AAC | 4693 |
| Ala | Gly | Phe | Asn | Met | Thr | Cys | Asn | Ile | Asp | Gln | Val | Val | Pro | Ala | Asn | |
| | 1485 | | | | | 1490 | | | | | 1495 | | | | | |
| GAC | CCC | GTC | ACC | GGC | GTG | GCG | CTG | GAG | CAC | AGC | ACG | CAG | ATG | GCG | GCC | 4741 |
| Asp | Pro | Val | Thr | Gly | Val | Ala | Leu | Glu | His | Ser | Thr | Gln | Met | Ala | Ala | |
| 1500 | | | | 1505 | | | | | | 1510 | | | | | 1515 | |
| ACT | TCA | TAC | GGG | ACA | ACG | TAC | CCG | TAC | TCG | CTG | ATG | AGA | TAGACAGATC | | | 4790 |
| Thr | Ser | Tyr | Gly | Thr | Thr | Tyr | Pro | Tyr | Ser | Leu | Met | Arg | | | | |
| | | | 1520 | | | | | 1525 | | | | | | | | |

| | | | | |
|---|---|---|---|---|
| CGTAGTGACC | TAGTCCTCCT | GAGCTCGATA | CAAACAACGC | TGGCGGCGCG | ATCGTGGTGT | 4850 |
| TGCAGGACTT | GTTGACCAAC | TCCAGCCCGG | ACTTCGGCGC | CTGACTCGAG | CCTGCACGGT | 4910 |
| GTACGTCTGG | CCTCACTGTC | TGCTGTGCTC | GGTTTCATGT | GCCTTGTGCT | ACTGCTTACC | 4970 |
| TTCATCATCA | GGACTAGAGC | GCTAAACCGA | CGGTTGGAAG | CCCTGTCGAT | GACGAAGTAC | 5030 |
| GGCTCACTGG | ACTCTGGATT | GAACCGCGCC | GGCATCGCCG | CCCCGGCAC | CAACAAACAC | 5090 |
| ACTGTGGAAG | GCTCCAACCC | TATCTTCAAT | GAAGCAATAA | AGACGCCAGA | TTTAGATGCC | 5150 |
| ATTAGCGAGG | GTTCCAACGA | CTCTGATCTG | ATCGGCATCG | AAGATCTTGC | GCACTTTGGC | 5210 |
| AACGTCTTCA | TGGATCCTGA | GGTGAACGAA | AAGGCAAATG | GTTATCCCGA | AGTCGCAAAC | 5270 |
| CACAACAACA | ACTTCGCTTT | CAACCCGACT | CCCTTCTCGC | CTGAGTTCGT | TAACGGACAG | 5330 |
| TTCAGAAAGA | TCTAGAAGAT | AACAACACTA | GTTAAGATCA | TTAATTTTGG | AGTTTGGAAT | 5390 |
| TAAGATTTTT | GAAAGGATAG | TTGTGATAAG | CCTGTGATTT | TTAAAACTGT | AATTGAAAAA | 5450 |
| AAAAATTGAG | ACCTCCATTT | AAGCTCTTGC | TCTCATCTCA | TCAAATTTTA | TAAAATGCCA | 5510 |
| TTAGTCATTA | AGATACTCGA | TTTAATTTAA | GATTATTTAA | GATATTATGT | AAAATAAATA | 5570 |
| TATTGTC | | | | | | 5577 |

( 2 ) INFORMATION FOR SEQ ID NO:2:

( i ) SEQUENCE CHARACTERISTICS:
        ( A ) LENGTH: 1528 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ala Val Asp Val Arg Ile Ala Ala Phe Leu Leu Val Phe Ile Ala
 1               5                  10                 15
Pro Ala Val Leu Ala Gln Glu Arg Cys Gly Tyr Met Thr Ala Ile Pro
             20                  25                 30
Arg Leu Pro Arg Pro Asp Asn Leu Pro Val Leu Asn Phe Glu Gly Gln
         35                  40                 45
Thr Trp Ser Gln Arg Pro Leu Leu Pro Ala Pro Glu Arg Asp Asp Leu
     50                  55                 60
Cys Met Asp Ala Tyr His Val Ile Thr Ala Asn Leu Gly Thr Gln Val
 65                  70                 75                 80
Ile Tyr Met Asp Glu Glu Ile Glu Asp Glu Ile Thr Ile Ala Ile Leu
                 85                  90                 95
Asn Tyr Asn Gly Pro Ser Thr Pro Phe Ile Glu Leu Pro Phe Leu Ser
             100                 105                110
Gly Ser Tyr Asn Leu Leu Met Pro Val Ile Arg Arg Val Asp Asn Gly
         115                 120                125
Ser Ala Ser His His His Ala Arg Gln His Tyr Glu Leu Pro Gly Met
     130                 135                 140
Gln Gln Tyr Met Phe Asn Val Arg Val Asp Gly Gln Ser Leu Val Ala
145                 150                 155                160
Gly Val Ser Leu Ala Ile Val Asn Ile Asp Asp Asn Ala Pro Ile Ile
                 165                 170                175
Gln Asn Phe Glu Pro Cys Arg Val Pro Glu Leu Gly Glu Pro Gly Leu
             180                 185                190
Thr Glu Cys Thr Tyr Gln Val Ser Asp Ala Asp Gly Arg Ile Ser Thr
         195                 200                205
Glu Phe Met Thr Phe Arg Ile Asp Ser Val Arg Gly Asp Glu Glu Thr
     210                 215                 220
Phe Tyr Ile Glu Arg Thr Asn Ile Pro Asn Gln Trp Met Trp Leu Asn
225                 230                 235                240
Met Thr Ile Gly Val Asn Thr Ser Leu Asn Phe Val Thr Ser Pro Leu
                 245                 250                255
His Ile Phe Ser Val Thr Ala Leu Asp Ser Leu Pro Asn Thr His Thr
             260                 265                270
Val Thr Met Met Val Gln Val Ala Asn Val Asn Ser Arg Pro Pro Arg
         275                 280                285
Trp Leu Glu Ile Phe Ala Val Gln Gln Phe Glu Glu Lys Ser Tyr Gln
     290                 295                 300
Asn Phe Thr Val Arg Ala Ile Asp Gly Asp Thr Glu Ile Asn Met Pro
305                 310                 315                320
Ile Asn Tyr Arg Leu Ile Thr Asn Glu Glu Asp Thr Phe Phe Ser Ile
                 325                 330                335
Glu Ala Leu Pro Gly Gly Lys Ser Gly Ala Val Phe Leu Val Ser Pro
             340                 345                350
Ile Asp Arg Asp Thr Leu Gln Arg Glu Val Phe Pro Leu Thr Ile Val
```

|     | 355 |     |     |     | 360 |     |     |     | 365 |     |     |     |
|-----|-----|-----|-----|-----|-----|-----|-----|-----|-----|-----|-----|-----|

Ala Tyr Lys Tyr Asp Glu Glu Ala Phe Ser Thr Ser Thr Asn Val Val
370                     375                 380

Ile Ile Val Thr Asp Ile Asn Asp Gln Arg Pro Glu Pro Ile His Lys
385                     390                 395                 400

Glu Tyr Arg Leu Ala Ile Met Glu Glu Thr Pro Leu Thr Leu Asn Phe
                405                 410                 415

Asp Lys Glu Phe Gly Phe His Asp Lys Asp Leu Gly Gln Asn Ala Gln
            420                 425                 430

Tyr Thr Val Arg Leu Glu Ser Val Asp Pro Pro Gly Ala Ala Glu Ala
        435                 440                 445

Phe Tyr Ile Ala Pro Glu Val Gly Tyr Gln Arg Gln Thr Phe Ile Met
    450                 455                 460

Gly Thr Leu Asn His Ser Met Leu Asp Tyr Glu Val Pro Glu Phe Gln
465                 470                 475                 480

Ser Ile Thr Ile Arg Val Val Ala Thr Asp Asn Asn Asp Thr Arg His
                485                 490                 495

Val Gly Val Ala Leu Val His Ile Asp Leu Ile Asn Trp Asn Asp Glu
            500                 505                 510

Gln Pro Ile Phe Glu His Ala Val Gln Thr Val Thr Phe Asp Glu Thr
        515                 520                 525

Glu Gly Glu Gly Phe Phe Val Ala Lys Ala Val Ala His Asp Arg Asp
    530                 535                 540

Ile Gly Asp Val Val Glu His Thr Leu Leu Gly Asn Ala Val Asn Phe
545                 550                 555                 560

Leu Thr Ile Asp Lys Leu Thr Gly Asp Ile Arg Val Ser Ala Asn Asp
                565                 570                 575

Ser Phe Asn Tyr His Arg Glu Ser Glu Leu Phe Val Gln Val Arg Ala
            580                 585                 590

Thr Asp Thr Leu Gly Glu Pro Phe His Thr Ala Thr Ser Gln Leu Val
        595                 600                 605

Ile Arg Leu Asn Asp Ile Asn Asn Thr Pro Pro Thr Leu Arg Leu Pro
    610                 615                 620

Arg Gly Ser Pro Gln Val Glu Glu Asn Val Pro Asp Gly His Val Ile
625                 630                 635                 640

Thr Gln Glu Leu Arg Ala Thr Asp Pro Asp Thr Thr Ala Asp Leu Arg
                645                 650                 655

Phe Glu Ile Asn Trp Asp Thr Ser Phe Ala Thr Lys Gln Gly Arg Gln
            660                 665                 670

Ala Asn Pro Asp Glu Phe Arg Asn Cys Val Glu Ile Glu Thr Ile Phe
        675                 680                 685

Pro Glu Ile Asn Asn Arg Gly Leu Ala Ile Gly Arg Val Val Ala Arg
    690                 695                 700

Glu Ile Arg His Asn Val Thr Ile Asp Tyr Glu Glu Phe Glu Val Leu
705                 710                 715                 720

Ser Leu Thr Val Arg Val Arg Asp Leu Asn Thr Val Tyr Gly Asp Asp
                725                 730                 735

Tyr Asp Glu Ser Met Leu Thr Ile Thr Ile Ile Asp Met Asn Asp Asn
            740                 745                 750

Ala Pro Val Trp Val Glu Gly Thr Leu Glu Gln Asn Phe Arg Val Arg
        755                 760                 765

Glu Met Ser Ala Gly Gly Leu Val Val Gly Ser Val Arg Ala Asp Asp
    770                 775                 780

```
Ile  Asp  Gly  Pro  Leu  Tyr  Asn  Gln  Val  Arg  Tyr  Thr  Ile  Phe  Pro  Arg
785                 790                 795                           800

Glu  Asp  Thr  Asp  Lys  Asp  Leu  Ile  Met  Ile  Asp  Phe  Leu  Thr  Gly  Gln
                    805                 810                      815

Ile  Ser  Val  Asn  Thr  Ser  Gly  Ala  Ile  Asp  Ala  Asp  Thr  Pro  Pro  Arg
               820                 825                      830

Phe  His  Leu  Tyr  Tyr  Thr  Val  Val  Ala  Ser  Asp  Arg  Cys  Ser  Thr  Glu
          835                 840                      845

Asp  Pro  Ala  Asp  Cys  Pro  Pro  Asp  Pro  Thr  Tyr  Trp  Glu  Thr  Glu  Gly
     850                 855                      860

Asn  Ile  Thr  Ile  His  Ile  Thr  Asp  Thr  Asn  Asn  Lys  Val  Pro  Gln  Ala
865                 870                      875                           880

Glu  Thr  Thr  Lys  Phe  Asp  Thr  Val  Val  Tyr  Ile  Tyr  Glu  Asn  Ala  Thr
                    885                      890                           895

His  Leu  Asp  Glu  Val  Val  Thr  Leu  Ile  Ala  Ser  Asp  Leu  Asp  Arg  Asp
               900                 905                      910

Glu  Ile  Tyr  His  Thr  Val  Ser  Tyr  Val  Ile  Asn  Tyr  Ala  Val  Asn  Pro
          915                 920                      925

Arg  Leu  Met  Asn  Phe  Phe  Ser  Val  Asn  Arg  Glu  Thr  Gly  Leu  Val  Tyr
930                      935                      940

Val  Asp  Tyr  Glu  Thr  Gln  Gly  Ser  Gly  Glu  Val  Leu  Asp  Arg  Asp  Gly
945                 950                      955                           960

Asp  Glu  Pro  Thr  His  Arg  Ile  Phe  Phe  Asn  Leu  Ile  Asp  Asn  Phe  Met
                    965                      970                      975

Gly  Glu  Gly  Glu  Gly  Asn  Arg  Asn  Gln  Asn  Asp  Thr  Glu  Val  Leu  Val
               980                 985                      990

Ile  Leu  Leu  Asp  Val  Asn  Asp  Asn  Ala  Pro  Glu  Leu  Pro  Pro  Pro  Ser
          995                 1000                     1005

Glu  Leu  Ser  Trp  Thr  Ile  Ser  Glu  Asn  Leu  Lys  Gln  Gly  Val  Arg  Leu
     1010                     1015                     1020

Glu  Pro  His  Ile  Phe  Ala  Pro  Asp  Arg  Asp  Glu  Pro  Asp  Thr  Asp  Asn
1025                     1030                     1035                     1040

Ser  Arg  Val  Gly  Tyr  Glu  Ile  Leu  Asn  Leu  Ser  Thr  Glu  Arg  Asp  Ile
                    1045                     1050                     1055

Glu  Val  Pro  Glu  Leu  Phe  Val  Met  Ile  Gln  Ile  Ala  Asn  Val  Thr  Gly
               1060                     1065                     1070

Glu  Leu  Glu  Thr  Ala  Met  Asp  Leu  Lys  Gly  Tyr  Trp  Gly  Thr  Tyr  Ala
          1075                     1080                     1085

Ile  His  Ile  Arg  Ala  Phe  Asp  His  Gly  Ile  Pro  Gln  Met  Ser  Met  Asn
     1090                     1095                     1100

Glu  Thr  Tyr  Glu  Leu  Ile  Ile  His  Pro  Phe  Asn  Tyr  Tyr  Ala  Pro  Glu
1105                     1110                     1115                     1120

Phe  Val  Phe  Pro  Thr  Asn  Asp  Ala  Val  Ile  Arg  Leu  Ala  Arg  Glu  Arg
                    1125                     1130                     1135

Ala  Val  Ile  Asn  Gly  Val  Leu  Ala  Thr  Val  Asn  Gly  Glu  Phe  Leu  Glu
               1140                     1145                     1150

Arg  Ile  Ser  Ala  Thr  Asp  Pro  Asp  Gly  Leu  His  Ala  Gly  Val  Val  Thr
          1155                     1160                     1165

Phe  Gln  Val  Val  Gly  Asp  Glu  Glu  Ser  Gln  Arg  Tyr  Phe  Gln  Val  Val
     1170                     1175                     1180

Asn  Asp  Gly  Glu  Asn  Leu  Gly  Ser  Leu  Arg  Leu  Leu  Gln  Ala  Val  Pro
1185                     1190                     1195                     1200

Glu  Glu  Ile  Arg  Glu  Phe  Arg  Ile  Thr  Ile  Arg  Ala  Thr  Asp  Gln  Gly
                    1205                     1210                     1215
```

Thr Asp Pro Gly Pro Leu Ser Thr Asp Met Thr Phe Arg Val Val Phe
          1220                1225                1230

Val Pro Thr Gln Gly Glu Pro Arg Phe Ala Ser Ser Glu His Ala Val
          1235                1240                1245

Ala Phe Ile Glu Lys Ser Ala Gly Met Glu Glu Ser His Gln Leu Pro
          1250                1255                1260

Leu Ala Gln Asp Ile Lys Asn His Leu Cys Glu Asp Asp Cys His Ser
1265                1270                1275                1280

Ile Tyr Tyr Arg Ile Ile Asp Gly Asn Ser Glu Gly His Phe Gly Leu
              1285                1290                1295

Asp Pro Val Arg Asn Arg Leu Phe Leu Lys Lys Glu Leu Ile Arg Glu
          1300                1305                1310

Gln Ser Ala Ser His Thr Leu Gln Val Ala Ala Ser Asn Ser Pro Asp
          1315                1320                1325

Gly Gly Ile Pro Leu Pro Ala Ser Ile Leu Thr Val Thr Val Thr Val
          1330                1335                1340

Arg Glu Ala Asp Pro Arg Pro Val Phe Val Arg Glu Leu Tyr Thr Ala
1345                1350                1355                1360

Gly Ile Ser Thr Ala Asp Ser Ile Gly Arg Glu Leu Leu Arg Leu His
                  1365                1370                1375

Ala Thr Gln Ser Glu Gly Ser Ala Ile Thr Tyr Ala Ile Asp Tyr Asp
          1380                1385                1390

Thr Met Val Val Asp Pro Ser Leu Glu Ala Val Arg Gln Ser Ala Phe
          1395                1400                1405

Val Leu Asn Ala Gln Thr Gly Val Leu Thr Leu Asn Ile Gln Pro Thr
          1410                1415                1420

Ala Thr Met His Gly Leu Phe Lys Phe Glu Val Thr Ala Thr Asp Thr
1425                1430                1435                1440

Ala Gly Ala Gln Asp Arg Thr Asp Val Thr Val Tyr Val Val Ser Ser
              1445                1450                1455

Gln Asn Arg Val Tyr Phe Val Phe Val Asn Thr Leu Gln Gln Val Glu
              1460                1465                1470

Asp Asn Arg Asp Phe Ile Ala Asp Thr Phe Ser Ala Gly Phe Asn Met
          1475                1480                1485

Thr Cys Asn Ile Asp Gln Val Val Pro Ala Asn Asp Pro Val Thr Gly
          1490                1495                1500

Val Ala Leu Glu His Ser Thr Gln Met Ala Ala Thr Ser Tyr Gly Thr
1505                1510                1515                1520

Thr Tyr Pro Tyr Ser Leu Met Arg
              1525

( 2 ) INFORMATION FOR SEQ ID NO:3:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Glu Trp Val Met Pro Pro Ile Phe Val Pro Glu Asn Gly Lys Gly Pro
1              5                  10                  15

Phe Pro Gln Arg Leu Asn Gln Leu Lys Ser Asn Lys Asp Arg Gly Thr
              20                  25                  30

Lys Ile Phe Tyr Tyr Ser Ile Thr Gly Pro Gly Ala Asp Ser Pro Pro
              35                  40                  45

```
Glu  Gly  Val  Phe  Thr  Ile  Glu  Lys  Glu  Ser  Gly  Trp  Leu  Leu  Leu  His
     50                      55                     60

Met  Pro  Leu  Asp  Arg  Glu  Lys  Ile  Val  Lys  Tyr  Glu  Leu  Tyr  Gly  His
65                       70                      75                          80

Ala  Val  Ser  Glu  Asn  Gly  Ala  Ser  Val  Glu  Glu  Pro  Met  Asn  Ile  Ser
               85                       90                            95

Ile  Ile  Val  Thr  Asp  Gln  Asn  Asp  Asn  Lys  Pro
               100                 105
```

(2) INFORMATION FOR SEQ ID NO:4:

(i) SEQUENCE CHARACTERISTICS:
        (A) LENGTH: 105 amino acids
        (B) TYPE: amino acid
        (C) STRANDEDNESS: single
        (D) TOPOLOGY: linear (xi) SEQUENCE DESCRIPTION: SEQ ID NO:4:

```
Glu  Asp  Thr  Val  Tyr  Ser  Phe  Asp  Ile  Asp  Glu  Asn  Ala  Gln  Arg  Gly
1                   5                       10                      15

Tyr  Gln  Val  Gly  Gln  Ile  Val  Ala  Arg  Asp  Ala  Asp  Leu  Gly  Gln  Asn
               20                      25                      30

Ala  Gln  Leu  Ser  Tyr  Gly  Val  Val  Ser  Asp  Trp  Ala  Asn  Asp  Val  Phe
               35                      40                      45

Ser  Leu  Asn  Pro  Gln  Thr  Gly  Met  Leu  Thr  Leu  Thr  Ala  Arg  Leu  Asp
     50                      55                     60

Tyr  Glu  Glu  Val  Gln  His  Tyr  Ile  Leu  Ile  Val  Gln  Ala  Gln  Asp  Asn
65                       70                      75                          80

Gly  Gln  Pro  Ser  Leu  Ser  Thr  Thr  Ile  Thr  Val  Tyr  Cys  Asn  Val  Leu
               85                       90                            95

Asp  Leu  Asn  Asp  Asn  Ala  Pro  Ile  Phe
               100                 105
```

(2) INFORMATION FOR SEQ ID NO:5:

(i) SEQUENCE CHARACTERISTICS:
        (A) LENGTH: 93 amino acids
        (B) TYPE: amino acid
        (C) STRANDEDNESS: single
        (D) TOPOLOGY: linear (xi) SEQUENCE DESCRIPTION: SEQ ID NO:5:

```
Ala  Ser  Pro  Val  Ile  Thr  Leu  Ala  Ile  Pro  Glu  Asn  Thr  Asn  Ile  Gly
1                   5                       10                      15

Ser  Leu  Phe  Pro  Ile  Pro  Leu  Ala  Ser  Asp  Arg  Asp  Ala  Asn  Glu  Leu
               20                      25                      30

Gln  Val  Ala  Glu  Asp  Gln  Glu  Lys  Gln  Pro  Gln  Leu  Ile  Val  Met
               35                      40                      45

Gly  Asn  Leu  Asp  Arg  Glu  Arg  Trp  Asp  Ser  Tyr  Asp  Leu  Thr  Ile  Lys
     50                      55                     60

Val  Gln  Asp  Gly  Gly  Ser  Pro  Pro  Arg  Ala  Thr  Ser  Ala  Leu  Leu  Arg
65                       70                      75                          80

Val  Thr  Val  Leu  Asp  Thr  Asn  Asp  Asn  Ala  Pro  Lys  Phe
               85                       90
```

(2) INFORMATION FOR SEQ ID NO:6:

(i) SEQUENCE CHARACTERISTICS:
        (A) LENGTH: 106 amino acids
        (B) TYPE: amino acid ( C ) STRANDEDNESS: single
( D ) TOPOLOGY: linear ( x i ) SEQUENCE DESCRIPTION: SEQ ID NO:6:

| Ile | Val | Thr | Glu | Asn | Ile | Trp | Lys | Ala | Pro | Lys | Pro | Val | Glu | Met | Val |
|---|---|---|---|---|---|---|---|---|---|---|---|---|---|---|---|
| 1 | | | | 5 | | | | | 10 | | | | | 15 | |

| Glu | Asn | Ser | Thr | Pro | His | Pro | Ile | Lys | Ile | Thr | Gln | Val | Arg | Trp | Asn |
|---|---|---|---|---|---|---|---|---|---|---|---|---|---|---|---|
| | | | 20 | | | | | 25 | | | | | 30 | | |

| Asp | Pro | Gly | Ala | Gln | Tyr | Ser | Leu | Val | Asp | Lys | Glu | Lys | Leu | Pro | Arg |
|---|---|---|---|---|---|---|---|---|---|---|---|---|---|---|---|
| | | 35 | | | | | 40 | | | | 45 | | | | |

| Phe | Pro | Phe | Ser | Ile | Asp | Gln | Glu | Gly | Asp | Ile | Tyr | Val | Thr | Pro | Leu |
|---|---|---|---|---|---|---|---|---|---|---|---|---|---|---|---|
| | 50 | | | | | 55 | | | | | 60 | | | | |

| Asp | Arg | Glu | Glu | Lys | Asp | Ala | Tyr | Val | Phe | Tyr | Ala | Val | Ala | Lys | Asp |
|---|---|---|---|---|---|---|---|---|---|---|---|---|---|---|---|
| 65 | | | | | 70 | | | | | 75 | | | | | 80 |

| Glu | Tyr | Gly | Lys | Pro | Leu | Ser | Tyr | Pro | Leu | Glu | Ile | His | Val | Lys | Val |
|---|---|---|---|---|---|---|---|---|---|---|---|---|---|---|---|
| | | | | 85 | | | | | 90 | | | | | 95 | |

| Lys | Asp | Ile | Asn | Asp | Asn | Pro | Pro | Thr | Cys |
|---|---|---|---|---|---|---|---|---|---|
| | | | 100 | | | | | 105 | |

( 2 ) INFORMATION FOR SEQ ID NO:7:

( i ) SEQUENCE CHARACTERISTICS:
( A ) LENGTH: 105 amino acids
( B ) TYPE: amino acid
( C ) STRANDEDNESS: single
( D ) TOPOLOGY: linear ( x i ) SEQUENCE DESCRIPTION: SEQ ID NO:7:

| Ile | Thr | Ala | Asn | Leu | Gly | Thr | Gln | Val | Ile | Tyr | Met | Asp | Glu | Glu | Ile |
|---|---|---|---|---|---|---|---|---|---|---|---|---|---|---|---|
| 1 | | | | 5 | | | | | 10 | | | | | 15 | |

| Glu | Asp | Glu | Ile | Thr | Ile | Ala | Ile | Leu | Asn | Tyr | Asn | Gly | Pro | Ser | Thr |
|---|---|---|---|---|---|---|---|---|---|---|---|---|---|---|---|
| | | | 20 | | | | | 25 | | | | | 30 | | |

| Pro | Phe | Ile | Glu | Leu | Pro | Phe | Leu | Ser | Gly | Ser | Tyr | Asn | Leu | Leu | Met |
|---|---|---|---|---|---|---|---|---|---|---|---|---|---|---|---|
| | | | 35 | | | | | 40 | | | | | 45 | | |

| Pro | Val | Ile | Arg | Arg | Val | Asp | Asn | Gly | Ser | Ala | Ser | His | His | His | Ala |
|---|---|---|---|---|---|---|---|---|---|---|---|---|---|---|---|
| | | 50 | | | | | 55 | | | | | 60 | | | |

| Arg | Gln | His | Tyr | Glu | Leu | Pro | Gly | Met | Gln | Gln | Tyr | Met | Phe | Asn | Val |
|---|---|---|---|---|---|---|---|---|---|---|---|---|---|---|---|
| 65 | | | | | 70 | | | | | 75 | | | | | 80 |

| Arg | Val | Asp | Gly | Gln | Ser | Leu | Val | Ala | Gly | Val | Ser | Leu | Ala | Ile | Val |
|---|---|---|---|---|---|---|---|---|---|---|---|---|---|---|---|
| | | | | 85 | | | | | 90 | | | | | 95 | |

| Asn | Ile | Asp | Asp | Asn | Ala | Pro | Ile | Ile |
|---|---|---|---|---|---|---|---|---|
| | | | 100 | | | | | 105 |

( 2 ) INFORMATION FOR SEQ ID NO:8:

( i ) SEQUENCE CHARACTERISTICS:
( A ) LENGTH: 113 amino acids
( B ) TYPE: amino acid
( C ) STRANDEDNESS: single
( D ) TOPOLOGY: linear ( x i ) SEQUENCE DESCRIPTION: SEQ ID NO:8:

| Gln | Asn | Phe | Glu | Pro | Cys | Arg | Val | Pro | Glu | Leu | Gly | Glu | Pro | Gly | Leu |
|---|---|---|---|---|---|---|---|---|---|---|---|---|---|---|---|
| 1 | | | | 5 | | | | | 10 | | | | | 15 | |

| Thr | Glu | Cys | Thr | Tyr | Gln | Val | Ser | Ala | Asp | Gly | Arg | Ile | Ser | Thr |
|---|---|---|---|---|---|---|---|---|---|---|---|---|---|---|
| | | | 20 | | | | | 25 | | | | | 30 | |

| Glu | Phe | Met | Thr | Phe | Arg | Ile | Asp | Ser | Val | Arg | Gly | Asp | Glu | Glu | Thr |
|---|---|---|---|---|---|---|---|---|---|---|---|---|---|---|---|
| | | | 35 | | | | | 40 | | | | | 45 | | |

| Phe | Tyr | Ile | Glu | Arg | Thr | Asn | Ile | Pro | Asn | Gln | Trp | Met | Trp | Leu | Asn |
|---|---|---|---|---|---|---|---|---|---|---|---|---|---|---|---|
| | | | 50 | | | | | 55 | | | | | 60 | | |

```
Met  Thr  Ile  Gly  Val  Asn  Thr  Ser  Leu  Asn  Phe  Val  Thr  Ser  Pro  Leu
65             70                  75                  80

His  Ile  Phe  Ser  Val  Thr  Ala  Leu  Asp  Ser  Leu  Pro  Asn  Thr  His  Thr
                85                  90                  95

Val  Thr  Met  Met  Val  Gln  Val  Ala  Asn  Val  Asn  Ser  Arg  Pro  Pro  Arg
               100                 105                 110

Trp
```

(2) INFORMATION FOR SEQ ID NO:9:

(i) SEQUENCE CHARACTERISTICS:
        (A) LENGTH: 106 amino acids
        (B) TYPE: amino acid
        (C) STRANDEDNESS: single
        (D) TOPOLOGY: linear (xi) SEQUENCE DESCRIPTION: SEQ ID NO:9:

```
Leu  Glu  Ile  Phe  Ala  Val  Gln  Gln  Phe  Glu  Glu  Lys  Ser  Tyr  Gln  Asn
1              5                   10                  15

Phe  Thr  Val  Arg  Ala  Ile  Asp  Gly  Asp  Thr  Glu  Ile  Asn  Met  Pro  Ile
               20                  25                  30

Asn  Tyr  Arg  Leu  Ile  Thr  Asn  Glu  Glu  Asp  Thr  Phe  Phe  Ser  Ile  Glu
          35                  40                  45

Ala  Leu  Pro  Gly  Gly  Lys  Ser  Gly  Ala  Val  Phe  Leu  Val  Ile  Asp  Arg
     50                  55                       60

Asp  Thr  Leu  Gln  Arg  Glu  Val  Phe  Pro  Leu  Thr  Ile  Val  Ala  Tyr  Lys
65                  70                  75                  80

Tyr  Asp  Glu  Glu  Ala  Phe  Ser  Thr  Ser  Thr  Asn  Val  Val  Ile  Ile  Val
               85                  90                  95

Thr  Asp  Ile  Asn  Asp  Gln  Arg  Pro  Glu  Pro
               100                 105
```

(2) INFORMATION FOR SEQ ID NO:10:

(i) SEQUENCE CHARACTERISTICS:
        (A) LENGTH: 119 amino acids
        (B) TYPE: amino acid
        (C) STRANDEDNESS: single
        (D) TOPOLOGY: linear (xi) SEQUENCE DESCRIPTION: SEQ ID NO:10:

```
Ile  His  Lys  Glu  Tyr  Arg  Leu  Ala  Ile  Met  Glu  Glu  Thr  Pro  Leu  Thr
1              5                   10                  15

Leu  Asn  Phe  Asp  Lys  Glu  Phe  Gly  Phe  His  Asp  Lys  Asp  Leu  Gly  Gln
               20                  25                  30

Asn  Ala  Gln  Tyr  Thr  Val  Arg  Leu  Glu  Ser  Val  Asp  Pro  Pro  Gly  Ala
          35                  40                  45

Ala  Glu  Ala  Phe  Tyr  Ile  Ala  Pro  Glu  Val  Gly  Tyr  Gln  Arg  Gln  Thr
     50                  55                       60

Phe  Ile  Met  Gly  Thr  Leu  Asn  His  Ser  Met  Leu  Asp  Tyr  Glu  Val  Pro
65                  70                  75                  80

Glu  Phe  Gln  Ser  Ile  Thr  Ile  Arg  Val  Val  Ala  Thr  Asp  Asn  Asn  Asp
               85                  90                  95

Thr  Arg  His  Val  Gly  Val  Ala  Leu  Val  His  Ile  Asp  Leu  Ile  Asn  Trp
               100                 105                 110

Asn  Asp  Glu  Gln  Pro  Ile  Phe
               115
```

( 2 ) INFORMATION FOR SEQ ID NO:11:

( i ) SEQUENCE CHARACTERISTICS:
        ( A ) LENGTH: 104 amino acids
        ( B ) TYPE: amino acid
        ( C ) STRANDEDNESS: single
        ( D ) TOPOLOGY: linear ( x i ) SEQUENCE DESCRIPTION: SEQ ID NO:11:

```
Glu His Ala Val Gln Thr Val Thr Phe Asp Glu Thr Glu Gly Glu Gly
 1               5                  10                 15
Phe Phe Val Ala Lys Ala Val Ala His Asp Arg Asp Ile Gly Asp Val
              20                 25                 30
Val Glu His Thr Leu Leu Gly Asn Ala Val Asn Phe Leu Thr Ile Asp
             35                 40                 45
Lys Leu Thr Gly Asp Ile Arg Val Ser Ala Asn Asp Ser Phe Tyr His
         50                 55                 60
Arg Glu Ser Glu Leu Phe Val Gln Val Arg Ala Thr Asp Thr Leu Gly
 65                 70                 75                 80
Gln Pro Phe His Thr Ala Thr Ser Gln Leu Val Ile Arg Leu Asn Asp
                 85                 90                 95
Ile Asn Asn Thr Pro Pro Thr Leu
             100
```

( 2 ) INFORMATION FOR SEQ ID NO:12:

( i ) SEQUENCE CHARACTERISTICS:
        ( A ) LENGTH: 138 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Arg Leu Pro Arg Gly Ser Pro Gln Val Glu Glu Asn Val Pro Asp Ala
 1               5                  10                 15
His Val Ile Thr Gln Glu Leu Arg Ala Thr Asp Pro Asp Thr Thr Ala
              20                 25                 30
Asp Leu Arg Phe Glu Ile Asn Trp Asp Thr Ser Phe Ala Thr Lys Gln
             35                 40                 45
Gly Arg Gln Ala Asn Pro Asp Glu Phe Arg Asn Cys Val Glu Ile Glu
         50                 55                 60
Thr Ile Phe Phe Pro Glu Ile Asn Asn Ile Asn Asn Arg Gly Leu Ala
 65                 70                 75                 80
Ile Gly Arg Val Val Ala Arg Glu Ile Arg His Asn Thr Ile Asp Tyr
                 85                 90                 95
Glu Glu Phe Glu Val Leu Ser Leu Thr Val Arg Val Arg Asp Leu Asn
             100                105                110
Thr Val Tyr Gly Asp Asp Tyr Asp Glu Ser Met Leu Thr Ile Thr Ile
             115                120                125
Ile Asp Met Asn Asp Asn Ala Pro Val Trp
         130                135
```

( 2 ) INFORMATION FOR SEQ ID NO:13:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

| Val | Glu | Gly | Thr | Leu | Glu | Gln | Asn | Phe | Arg | Val | Arg | Glu | Met | Ser | Ala |
| 1 | | | | 5 | | | | | 10 | | | | | 15 | |

| Gly | Gly | Leu | Val | Val | Gly | Ser | Val | Arg | Ala | Asp | Asp | Ile | Asp | Gly | Pro |
| | | | 20 | | | | | 25 | | | | | 30 | | |

| Leu | Tyr | Asn | Gln | Val | Arg | Tyr | Thr | Ile | Phe | Pro | Arg | Glu | Asp | Thr | Asp |
| | | 35 | | | | | 40 | | | | | 45 | | | |

| Lys | Asp | Leu | Ile | Met | Ile | Glu | Leu | Pro | His | Gly | Ser | Asn | Phe | Arg | Glu |
| | 50 | | | | | 55 | | | | | 60 | | | | |

| His | Lys | Arg | Arg | Ile | Asp | Ala | Asn | Thr | Pro | Pro | Arg | Phe | His | Leu | Tyr |
| 65 | | | | | 70 | | | | | 75 | | | | | 80 |

| Tyr | Thr | Val | Val | Ala | Ser | Asp | Arg | Cys | Ser | Thr | Glu | Asp | Pro | Ala | Asp |
| | | | | 85 | | | | | 90 | | | | | 95 | |

| Cys | Pro | Pro | Asp | Pro | Tyr | Tyr | Trp | Glu | Thr | Glu | Gly | Asn | Ile | Thr | Ile |
| | | | 100 | | | | | 105 | | | | | 110 | | |

| His | Ile | Thr | Asp | Thr | Asn | Asn | Lys | Val | Pro | Gln | Ala |
| | | 115 | | | | | 120 | | | | |

( 2 ) INFORMATION FOR SEQ ID NO:14:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

| Glu | Thr | Thr | Lys | Phe | Asp | Thr | Val | Val | Tyr | Ile | Tyr | Glu | Asn | Ala | Thr |
| 1 | | | | 5 | | | | | 10 | | | | | 15 | |

| His | Leu | Asp | Glu | Val | Val | Thr | Leu | Ile | Ala | Ser | Asp | Leu | Asp | Arg | Asp |
| | | | 20 | | | | | 25 | | | | | 30 | | |

| Glu | Ile | Tyr | His | Met | Val | Ser | Tyr | Val | Ile | Asn | Tyr | Ala | Val | Asn | Pro |
| | | | 35 | | | | | 40 | | | | | 45 | | |

| Arg | Leu | Met | Asn | Phe | Phe | Ser | Val | Asn | Arg | Glu | Thr | Gly | Leu | Val | Tyr |
| | | 50 | | | | | 55 | | | | | 60 | | | |

| Val | Asp | Tyr | Glu | Thr | Gln | Gly | Ser | Gly | Leu | Asp | Arg | Asp | Gly | Asp | Glu |
| 65 | | | | | 70 | | | | | 75 | | | | | 80 |

| Pro | Thr | His | Arg | Ile | Phe | Phe | Asn | Leu | Ile | Asp | Asn | Phe | Met | Gly | Glu |
| | | | | 85 | | | | | 90 | | | | | 95 | |

| Gly | Glu | Gly | Asn | Arg | Asn | Gln | Asn | Asp | Thr | Glu | Val | Leu | Val | Ile | Leu |
| | | | 100 | | | | | 105 | | | | | 110 | | |

| Leu | Asp | Val | Asn | Asp | Asn | Ala | Pro | Glu | Leu |
| | | 115 | | | | | 120 | | |

( 2 ) INFORMATION FOR SEQ ID NO:15:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

| Pro | Pro | Pro | Ser | Glu | Leu | Ser | Trp | Thr | Ile | Ser | Glu | Asn | Leu | Lys | Gln |
| 1 | | | | 5 | | | | | 10 | | | | | 15 | |

| Gly | Val | Arg | Leu | Glu | Pro | His | Ile | Phe | Ala | Pro | Asp | Arg | Asp | Glu | Pro |
| | | | 20 | | | | | 25 | | | | | 30 | | |

| Asp | Thr | Asp | Asn | Ser | Arg | Val | Gly | Tyr | Glu | Ile | Leu | Asn | Leu | Ser | Thr |
| | | | 35 | | | | | 40 | | | | | 45 | | |

| Glu | Arg | Asp | Ile | Glu | Val | Pro | Glu | Leu | Phe | Val | Met | Ile | Gln | Ile | Ile |

```
                  50                          55                          60
        Ala  Asn  Val  Thr  Gly  Tyr  Glu  Ile  Leu  Asn  Leu  Ser  Thr  Glu  Arg  Asp
        65                       70                       75                       80

Ile  Glu  Val  Pro  Glu  Leu  Phe  Val  Met  Ile  Gln  Ile  Ala  Asn  Val  Thr
                            85                       90                       95

Gly  Glu  Leu  Glu  Thr  Ala  Met  Asp  Leu  Lys  Gly  Tyr  Trp  Gly  Thr  Tyr
                            100                      105                      110

Ala  Ile  Tyr  Ile  Leu  Ala  Phe  Asp  His  Gly  Ile  Pro  Gln  Met  Ser  Met
                  115                      120                      125

Asn  Glu  Thr  Tyr  Glu  Leu  Ile  Ile  His  Pro  Phe  Asn  Tyr  Tyr  Ala  Pro
                  130                      135                      140

Glu  Phe
        145
```

( 2 ) INFORMATION FOR SEQ ID NO:16:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
        Val  Phe  Pro  Thr  Asn  Asp  Ala  Val  Ile  Arg  Leu  Ala  Arg  Glu  Arg  Ala
        1                        5                        10                       15

Val  Ile  Asn  Gly  Val  Leu  Ala  Thr  Val  Asn  Gly  Glu  Phe  Leu  Glu  Arg
                            20                       25                       30

Ile  Ser  Ala  Thr  Asp  Pro  Asp  Gly  Leu  His  Ala  Gly  Val  Val  Thr  Phe
                  35                       40                       45

Gln  Val  Gly  Asp  Glu  Glu  Ser  Gln  Arg  Tyr  Phe  Gln  Val  Val  Asp  Asn
                  50                       55                       60

Asp  Gly  Glu  Asn  Leu  Gly  Ser  Leu  Arg  Leu  Leu  Gln  Ala  Val  Pro  Glu
        65                       70                       75                       80

Glu  Ile  Arg  Glu  Phe  Arg  Ile  Thr  Ile  Arg  Ala  Thr  Asp  Gln  Gly  Thr
                            85                       90                       95

Asp  Pro  Gly  Pro  Leu  Ser  Thr  Asp  Met  Thr  Phe  Arg  Val  Val  Phe  Val
                            100                      105                      110

Pro  Thr  Gln  Gly  Glu  Pro  Arg  Phe
                  115                      120
```

( 2 ) INFORMATION FOR SEQ ID NO:17:

( i ) SEQUENCE CHARACTERISTICS:
        ( A ) LENGTH: 112 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

```
        Ala  Ser  Ser  Glu  His  Ala  Val  Ala  Phe  Ile  Glu  Lys  Ser  Ala  Gly  Met
        1                        5                        10                       15

Glu  Glu  Ser  His  Gln  Leu  Pro  Leu  Ala  Gln  Asp  Ile  Lys  Asn  His  Leu
                            20                       25                       30

Cys  Glu  Asp  Asp  Cys  His  Ser  Ile  Tyr  Tyr  Arg  Ile  Ile  Asp  Gly  Asn
                  35                       40                       45

Ser  Glu  Gly  His  Phe  Gly  Leu  Asp  Pro  Val  Arg  Asn  Arg  Leu  Phe  Leu
                  50                       55                       60

Lys  Lys  Glu  Leu  Ile  Arg  Glu  Gln  Ser  Ala  Ser  His  Thr  Leu  Gln  Val
        65                       70                       75                       80
```

```
Ala Ala Ser Asn Ser Pro Asp Gly Gly Ile Pro Leu Pro Ala Ser Ile
            85              90                  95

Leu Thr Val Thr Val Thr Val Arg Glu Ala Asp Pro Arg Pro Val Phe
            100             105                 110
```

( 2 ) INFORMATION FOR SEQ ID NO:18:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( x i ) SEQUENCE DESCRIPTION: SEQ ID NO:18:

```
Met Leu Asp Tyr Glu Val Pro Glu Phe Gln Ser Ile Thr Ile Arg Val
1               5                   10                  15

Val Ala Thr Asp Asn Asn Asp Thr Arg His Val Gly Val Ala
            20                  25                  30
```

( 2 ) INFORMATION FOR SEQ ID NO:19:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:19:

```
Met Xaa Glu Thr Tyr Glu Leu Ile Ile His Pro Phe Asn Tyr Tyr Ala
1               5                   10                  15
```

( 2 ) INFORMATION FOR SEQ ID NO:20:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

```
Met Xaa Xaa Xaa His Gln Leu Pro Leu Ala Gln Asp Ile Lys Asn His
1               5                   10                  15
```

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note= "This position is Phe/Pro"

( i x ) FEATURE:
        ( A ) NAME/KEY: Modified-site
        ( B ) LOCATION: 3
        ( D ) OTHER INFORMATION: /note= "This position is Asn/Ile"

( i x ) FEATURE:
        ( A ) NAME/KEY: Modified-site
        ( B ) LOCATION: 5
        ( D ) OTHER INFORMATION: /note= "This position is Arg/Tyr"

( i x ) FEATURE:
        ( A ) NAME/KEY: Modified-site
        ( B ) LOCATION: 8
        ( D ) OTHER INFORMATION: /note= "This position is Ile/Gly"

( x i ) SEQUENCE DESCRIPTION: SEQ ID NO:21:

Met Xaa Xaa Val Xaa Val Asp Xaa
1               5

( 2 ) INFORMATION FOR SEQ ID NO:22:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 4
        ( D ) OTHER INFORMATION: /note= "This position is Phe/His"

( i x ) FEATURE:
        ( A ) NAME/KEY: Modified-site
        ( B ) LOCATION: 8
        ( D ) OTHER INFORMATION: /note= "This position is Arg/Asp"

( x i ) SEQUENCE DESCRIPTION: SEQ ID NO:22:

Met Asn Phe Xaa Ser Val Asn Xaa Glu
1               5

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

Ala Xaa Asp Xaa Asp
1               5

( 2 ) INFORMATION FOR SEQ ID NO:24:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

Asp Xaa Asn Asp Xaa Xaa Pro
1               5

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /note= "Alanine(A) or Valine(V)"

( x i ) SEQUENCE DESCRIPTION: SEQ ID NO:25:

Xaa Xaa Asp Xaa Asp
1               5

( 2 ) INFORMATION FOR SEQ ID NO:26:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( x i ) SEQUENCE DESCRIPTION: SEQ ID NO:26:

Asp Xaa Asn Asp Asn
1               5